United States Patent
Schieber et al.

(10) Patent No.: US 8,808,222 B2
(45) Date of Patent: Aug. 19, 2014

(54) METHODS AND APPARATUS FOR DELIVERING OCULAR IMPLANTS INTO THE EYE

(71) Applicant: Ivantis, Inc., Irvine, CA (US)

(72) Inventors: Andrew T. Schieber, Irvine, CA (US); John Wardle, San Clemente, CA (US); Edward Matthees, Minneapolis, MN (US); Charles L. Euteneuer, St. Michael, MN (US)

(73) Assignee: Ivantis, Inc., Irvine, CA (US)

( * ) Notice: Subject to any disclaimer, the term of this patent is extended or adjusted under 35 U.S.C. 154(b) by 0 days.

(21) Appl. No.: 13/973,864

(22) Filed: Aug. 22, 2013

(65) Prior Publication Data

US 2013/0338563 A1  Dec. 19, 2013

Related U.S. Application Data

(60) Continuation of application No. 13/681,365, filed on Nov. 19, 2012, now Pat. No. 8,551,166, which is a division of application No. 12/632,738, filed on Dec. 7, 2009, now Pat. No. 8,337,509, which is a continuation of application No. 11/943,289, filed on Nov. 20, 2007, now Pat. No. 8,512,404.

(60) Provisional application No. 61/120,222, filed on Dec. 5, 2008, provisional application No. 61/120,295, filed on Dec. 5, 2008, provisional application No. 61/224,156, filed on Jul. 9, 2009, provisional application No. 61/224,158, filed on Jul. 9, 2009.

(51) Int. Cl.
*A61M 5/00* (2006.01)
*A61F 9/007* (2006.01)

(52) U.S. Cl.
CPC .................. *A61F 9/00781* (2013.01)
USPC ................................. 604/8; 623/6.12

(58) Field of Classification Search
USPC ............... 606/107, 108; 623/1.11, 1.23, 6.12; 604/272, 273, 274, 8
See application file for complete search history.

(56) References Cited

U.S. PATENT DOCUMENTS

| 3,788,327 A | 1/1974 | Donowitz et al. |
| 3,811,442 A | 5/1974 | Maroth |

(Continued)

FOREIGN PATENT DOCUMENTS

| AU | 1998/76197 B2 | 2/1999 |
| CN | 1950091 A | 4/2007 |

(Continued)

OTHER PUBLICATIONS

Bahler, et al.; Trabecular bypass stents decrease intraocular pressure in cultured human anterior segments; Amer. Journal of Ophthalmology; vol. 138, No. 6; pp. 988-994.e2; Dec. 2004.

(Continued)

*Primary Examiner* — Jonathan W Miles
(74) *Attorney, Agent, or Firm* — Shay Glenn LLP

(57) ABSTRACT

A method of deploying an ocular implant into Schlemm's canal of a human eye including the following steps: inserting a distal tip of a delivery tool within an anterior chamber of the eye through trabecular meshwork of the eye into Schlemm's canal of the eye; and advancing an ocular implant through a curved portion and a distal opening of the delivery tool to place a body portion of the ocular implant in Schlemm's canal and an inlet portion of the ocular implant in the anterior chamber.

4 Claims, 36 Drawing Sheets

(56) References Cited

U.S. PATENT DOCUMENTS

| | | |
|---|---|---|
| 3,948,271 A | 4/1976 | Akiyama |
| 4,037,604 A | 7/1977 | Newkirk |
| 4,428,746 A | 1/1984 | Mendez |
| 4,457,757 A | 7/1984 | Molteno |
| 4,722,724 A | 2/1988 | Schocket |
| 4,733,665 A | 3/1988 | Palmaz |
| 4,750,901 A | 6/1988 | Molteno |
| 4,826,478 A | 5/1989 | Schocket |
| 4,886,488 A | 12/1989 | White |
| 4,934,809 A | 6/1990 | Volk |
| 4,936,825 A | 6/1990 | Ungerleider |
| 4,946,436 A | 8/1990 | Smith |
| 4,968,296 A | 11/1990 | Ritch et al. |
| 5,092,837 A | 3/1992 | Ritch et al. |
| 5,127,901 A | 7/1992 | Odrich |
| 5,178,604 A | 1/1993 | Baerveldt et al. |
| 5,180,362 A | 1/1993 | Worst |
| 5,213,569 A | 5/1993 | Davis |
| 5,246,452 A | 9/1993 | Sinnott |
| 5,360,399 A | 11/1994 | Stegmann |
| 5,372,577 A | 12/1994 | Ungerleider |
| 5,454,796 A | 10/1995 | Krupin |
| 5,458,615 A | 10/1995 | Klemm et al. |
| 5,591,223 A | 1/1997 | Lock et al. |
| 5,626,558 A | 5/1997 | Suson |
| 5,792,099 A | 8/1998 | DeCamp et al. |
| 5,807,302 A | 9/1998 | Wandel |
| 5,865,831 A | 2/1999 | Cozean et al. |
| 5,868,697 A | 2/1999 | Richter et al. |
| 5,879,319 A | 3/1999 | Pynson et al. |
| 5,893,837 A | 4/1999 | Eagles et al. |
| 5,948,427 A | 9/1999 | Yamamoto et al. |
| 5,968,058 A | 10/1999 | Richter et al. |
| 6,007,511 A | 12/1999 | Prywes |
| 6,050,970 A | 4/2000 | Baerveldt |
| 6,102,045 A | 8/2000 | Nordquist et al. |
| 6,186,974 B1 | 2/2001 | Allan et al. |
| 6,221,078 B1 | 4/2001 | Bylsma |
| 6,238,409 B1 | 5/2001 | Hojeibane |
| D444,874 S | 7/2001 | Haffner et al. |
| 6,375,642 B1 | 4/2002 | Grieshaber et al. |
| 6,409,752 B1 | 6/2002 | Boatman et al. |
| 6,450,984 B1 | 9/2002 | Lynch et al. |
| 6,464,724 B1 | 10/2002 | Lynch et al. |
| 6,471,666 B1 | 10/2002 | Odrich |
| 6,494,857 B1 | 12/2002 | Neuhann |
| 6,508,779 B1 | 1/2003 | Suson |
| 6,524,275 B1 | 2/2003 | Lynch et al. |
| 6,533,764 B1 | 3/2003 | Haffner et al. |
| 6,533,768 B1 | 3/2003 | Hill |
| 6,544,208 B2 | 4/2003 | Ethier et al. |
| 6,544,249 B1 | 4/2003 | Yu et al. |
| 6,626,858 B2 | 9/2003 | Lynch et al. |
| 6,638,239 B1 | 10/2003 | Bergheim et al. |
| 6,666,841 B2 | 12/2003 | Gharib et al. |
| 6,699,210 B2 | 3/2004 | Williams et al. |
| 6,699,211 B2 | 3/2004 | Savage |
| 6,726,676 B2 | 4/2004 | Stegmann et al. |
| D490,152 S | 5/2004 | Myall et al. |
| 6,730,056 B1 | 5/2004 | Ghaem et al. |
| 6,736,791 B1 | 5/2004 | Tu et al. |
| 6,780,164 B2 | 8/2004 | Bergheim et al. |
| 6,783,544 B2 | 8/2004 | Lynch et al. |
| 6,827,699 B2 | 12/2004 | Lynch et al. |
| 6,827,700 B2 | 12/2004 | Lynch et al. |
| 6,881,198 B2 | 4/2005 | Brown |
| 6,939,298 B2 | 9/2005 | Brown et al. |
| 6,955,656 B2 | 10/2005 | Bergheim et al. |
| 6,962,573 B1 | 11/2005 | Wilcox |
| 6,981,958 B1 | 1/2006 | Gharib et al. |
| 6,989,007 B2 | 1/2006 | Shadduck |
| 7,094,225 B2 | 8/2006 | Tu et al. |
| 7,135,009 B2 | 11/2006 | Tu et al. |
| 7,147,650 B2 | 12/2006 | Lee |
| 7,163,543 B2 | 1/2007 | Smedley et al. |
| 7,186,232 B1 | 3/2007 | Smedley et al. |
| 7,192,412 B1 | 3/2007 | Zhou et al. |
| 7,207,965 B2 | 4/2007 | Simon |
| 7,207,980 B2 | 4/2007 | Christian et al. |
| 7,220,238 B2 | 5/2007 | Lynch et al. |
| 7,273,475 B2 | 9/2007 | Tu et al. |
| 7,297,130 B2 | 11/2007 | Bergheim et al. |
| 7,331,984 B2 | 2/2008 | Tu et al. |
| 7,699,882 B2 | 4/2010 | Stamper et al. |
| 7,740,604 B2 | 6/2010 | Schieber et al. |
| 7,931,596 B2 | 4/2011 | Rachlin et al. |
| 7,967,772 B2 | 6/2011 | McKenzie et al. |
| 8,012,115 B2 | 9/2011 | Karageozian |
| 8,034,105 B2 | 10/2011 | Stegmann et al. |
| 8,123,729 B2 | 2/2012 | Yamamoto et al. |
| 8,267,882 B2 | 9/2012 | Euteneuer et al. |
| 8,282,592 B2 | 10/2012 | Schieber et al. |
| 8,337,509 B2 | 12/2012 | Schieber et al. |
| 8,372,026 B2 | 2/2013 | Schieber et al. |
| 8,414,518 B2 | 4/2013 | Schieber et al. |
| 8,425,449 B2 | 4/2013 | Wardle et al. |
| 8,512,404 B2 | 8/2013 | Frion et al. |
| 8,529,494 B2 | 9/2013 | Euteneuer et al. |
| 8,551,166 B2 | 10/2013 | Schieber et al. |
| 8,636,647 B2 | 1/2014 | Silvestrini et al. |
| 2001/0002438 A1 | 5/2001 | Sepetka et al. |
| 2002/0003546 A1 | 1/2002 | Mochimaru et al. |
| 2002/0013546 A1 | 1/2002 | Grieshaber et al. |
| 2002/0013572 A1 | 1/2002 | Berlin |
| 2002/0072673 A1 | 6/2002 | Yamamoto et al. |
| 2002/0133168 A1 | 9/2002 | Smedley et al. |
| 2002/0143284 A1 | 10/2002 | Tu et al. |
| 2003/0004457 A1 | 1/2003 | Andersson |
| 2003/0055372 A1 | 3/2003 | Lynch et al. |
| 2003/0060748 A1 | 3/2003 | Baikoff |
| 2003/0060752 A1 | 3/2003 | Bergheim et al. |
| 2003/0093084 A1 | 5/2003 | Nissan et al. |
| 2003/0097151 A1 | 5/2003 | Smedley et al. |
| 2003/0181848 A1 | 9/2003 | Bergheim et al. |
| 2003/0187384 A1 | 10/2003 | Bergheim et al. |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0024345 A1 | 2/2004 | Gharib et al. |
| 2004/0024453 A1 | 2/2004 | Castillejos |
| 2004/0082939 A1 | 4/2004 | Berlin |
| 2004/0088048 A1 | 5/2004 | Richter et al. |
| 2004/0098124 A1 | 5/2004 | Freeman et al. |
| 2004/0102729 A1 | 5/2004 | Haffner et al. |
| 2004/0106975 A1 | 6/2004 | Solovay et al. |
| 2004/0111050 A1 | 6/2004 | Smedley et al. |
| 2004/0127843 A1 | 7/2004 | Tu et al. |
| 2004/0147870 A1 | 7/2004 | Burns et al. |
| 2004/0193095 A1 | 9/2004 | Shadduck |
| 2004/0193262 A1 | 9/2004 | Shadduck |
| 2004/0210181 A1 | 10/2004 | Vass et al. |
| 2004/0210185 A1 | 10/2004 | Tu et al. |
| 2004/0216749 A1 | 11/2004 | Tu |
| 2004/0225357 A1 | 11/2004 | Worst et al. |
| 2004/0249333 A1 | 12/2004 | Bergheim et al. |
| 2004/0254517 A1 | 12/2004 | Quiroz-Mercado et al. |
| 2004/0254519 A1 | 12/2004 | Tu et al. |
| 2004/0254520 A1 | 12/2004 | Porteous et al. |
| 2004/0260228 A1 | 12/2004 | Lynch et al. |
| 2005/0041200 A1 | 2/2005 | Rich |
| 2005/0049578 A1 | 3/2005 | Tu et al. |
| 2005/0090806 A1 | 4/2005 | Lynch et al. |
| 2005/0090807 A1 | 4/2005 | Lynch et al. |
| 2005/0101967 A1 | 5/2005 | Weber et al. |
| 2005/0107734 A1 | 5/2005 | Coroneo |
| 2005/0119601 A9 | 6/2005 | Lynch et al. |
| 2005/0119636 A1 | 6/2005 | Haffner et al. |
| 2005/0125003 A1 | 6/2005 | Pinchuk et al. |
| 2005/0131514 A1 | 6/2005 | Hijlkema et al. |
| 2005/0149114 A1 | 7/2005 | Cartledge et al. |
| 2005/0154443 A1 | 7/2005 | Linder et al. |
| 2005/0165385 A1 | 7/2005 | Simon |
| 2005/0192527 A1 | 9/2005 | Gharib et al. |
| 2005/0197667 A1 | 9/2005 | Chan et al. |

(56) References Cited

U.S. PATENT DOCUMENTS

| | | |
|---|---|---|
| 2005/0203542 A1 | 9/2005 | Weber et al. |
| 2005/0209549 A1 | 9/2005 | Bergheim et al. |
| 2005/0209550 A1 | 9/2005 | Bergheim et al. |
| 2005/0244464 A1 | 11/2005 | Hughes |
| 2005/0250788 A1 | 11/2005 | Tu et al. |
| 2005/0260186 A1 | 11/2005 | Bookbinder et al. |
| 2005/0266047 A1 | 12/2005 | Tu et al. |
| 2005/0271704 A1 | 12/2005 | Tu et al. |
| 2005/0273033 A1 | 12/2005 | Grahn et al. |
| 2005/0277864 A1 | 12/2005 | Haffner et al. |
| 2005/0288619 A1 | 12/2005 | Gharib et al. |
| 2005/0288745 A1 | 12/2005 | Andersen et al. |
| 2006/0020247 A1 | 1/2006 | Kagan et al. |
| 2006/0032507 A1 | 2/2006 | Tu |
| 2006/0052879 A1 | 3/2006 | Kolb |
| 2006/0069340 A1 | 3/2006 | Simon |
| 2006/0074375 A1 | 4/2006 | Bergheim et al. |
| 2006/0079828 A1 | 4/2006 | Brown |
| 2006/0084907 A1 | 4/2006 | Bergheim et al. |
| 2006/0106370 A1 | 5/2006 | Baerveldt et al. |
| 2006/0116626 A1 | 6/2006 | Smedley et al. |
| 2006/0149194 A1 | 7/2006 | Conston et al. |
| 2006/0154981 A1 | 7/2006 | Klimko et al. |
| 2006/0155238 A1 | 7/2006 | Shields |
| 2006/0155300 A1 | 7/2006 | Stamper et al. |
| 2006/0173397 A1 | 8/2006 | Tu et al. |
| 2006/0178674 A1 | 8/2006 | McIntyre |
| 2006/0189915 A1 | 8/2006 | Camras et al. |
| 2006/0189916 A1 | 8/2006 | Bas et al. |
| 2006/0189917 A1 | 8/2006 | Mayr et al. |
| 2006/0195055 A1 | 8/2006 | Bergheim et al. |
| 2006/0195056 A1 | 8/2006 | Bergheim et al. |
| 2006/0195187 A1 | 8/2006 | Stegmann et al. |
| 2006/0200113 A1 | 9/2006 | Haffner et al. |
| 2006/0241749 A1 | 10/2006 | Tu et al. |
| 2007/0010827 A1 | 1/2007 | Tu et al. |
| 2007/0027452 A1 | 2/2007 | Varner et al. |
| 2007/0073275 A1 | 3/2007 | Conston et al. |
| 2007/0088432 A1 | 4/2007 | Solovay et al. |
| 2007/0106200 A1 | 5/2007 | Levy |
| 2007/0106236 A1 | 5/2007 | Coroneo |
| 2007/0112292 A1 | 5/2007 | Tu et al. |
| 2007/0118147 A1 | 5/2007 | Smedley et al. |
| 2007/0179520 A1 | 8/2007 | West |
| 2007/0191863 A1 | 8/2007 | De Juan, Jr. et al. |
| 2007/0202186 A1 | 8/2007 | Yamamoto et al. |
| 2007/0265582 A1 | 11/2007 | Kaplan et al. |
| 2007/0270945 A1 | 11/2007 | Kobayashi et al. |
| 2007/0276315 A1 | 11/2007 | Haffner et al. |
| 2007/0276316 A1 | 11/2007 | Haffner et al. |
| 2007/0282244 A1 | 12/2007 | Tu et al. |
| 2007/0282245 A1 | 12/2007 | Tu et al. |
| 2007/0293807 A1 | 12/2007 | Lynch et al. |
| 2007/0293872 A1* | 12/2007 | Peyman .................. 606/107 |
| 2007/0298068 A1 | 12/2007 | Badawi et al. |
| 2008/0015488 A1 | 1/2008 | Tu et al. |
| 2008/0045878 A1 | 2/2008 | Bergheim et al. |
| 2008/0058704 A1 | 3/2008 | Hee et al. |
| 2008/0228127 A1 | 9/2008 | Burns et al. |
| 2009/0005852 A1 | 1/2009 | Gittings et al. |
| 2009/0028953 A1 | 1/2009 | Yamamoto et al. |
| 2009/0030363 A1 | 1/2009 | Gellman |
| 2009/0030381 A1 | 1/2009 | Lind et al. |
| 2009/0043321 A1 | 2/2009 | Conston et al. |
| 2009/0054723 A1 | 2/2009 | Khairkhahan et al. |
| 2009/0069786 A1 | 3/2009 | Vesely et al. |
| 2009/0082860 A1 | 3/2009 | Schieber et al. |
| 2009/0082862 A1 | 3/2009 | Schieber et al. |
| 2009/0104248 A1 | 4/2009 | Rapacki et al. |
| 2009/0138081 A1 | 5/2009 | Bergheim et al. |
| 2009/0182421 A1 | 7/2009 | Silvestrini et al. |
| 2009/0247955 A1 | 10/2009 | Yamamoto et al. |
| 2009/0281520 A1 | 11/2009 | Highley et al. |
| 2010/0004580 A1 | 1/2010 | Lynch et al. |
| 2010/0057072 A1 | 3/2010 | Roman et al. |
| 2010/0137981 A1 | 6/2010 | Silvestrini et al. |
| 2010/0173866 A1 | 7/2010 | Hee et al. |
| 2010/0191176 A1 | 7/2010 | Ho et al. |
| 2010/0191177 A1 | 7/2010 | Chang et al. |
| 2010/0234726 A1 | 9/2010 | Sirimanne et al. |
| 2010/0234790 A1 | 9/2010 | Tu et al. |
| 2011/0009874 A1 | 1/2011 | Wardle et al. |
| 2011/0098809 A1 | 4/2011 | Wardle et al. |
| 2011/0319806 A1 | 12/2011 | Wardle |
| 2012/0010702 A1 | 1/2012 | Stegmann et al. |
| 2012/0191064 A1 | 7/2012 | Conston et al. |
| 2012/0323159 A1 | 12/2012 | Wardle et al. |
| 2013/0150959 A1 | 6/2013 | Schieber et al. |
| 2013/0158462 A1 | 6/2013 | Wardle et al. |
| 2013/0172804 A1 | 7/2013 | Schieber et al. |
| 2013/0182223 A1 | 7/2013 | Wardle et al. |
| 2013/0231603 A1 | 9/2013 | Wardle et al. |
| 2013/0281907 A1 | 10/2013 | Wardle et al. |
| 2014/0066821 A1 | 3/2014 | Freidland et al. |
| 2014/0066831 A1 | 3/2014 | Silvestrini et al. |

FOREIGN PATENT DOCUMENTS

| | | |
|---|---|---|
| DE | 4226476 C1 | 8/1993 |
| EP | 1615604 B1 | 8/2009 |
| EP | 2193821 A1 | 6/2010 |
| EP | 1715827 B1 | 12/2010 |
| EP | 2380622 A1 | 10/2011 |
| EP | 2468327 A1 | 6/2012 |
| EP | 2471563 A1 | 7/2012 |
| EP | 1833440 B1 | 8/2012 |
| JP | H10-504978 A | 5/1998 |
| JP | 11123205 | 5/1999 |
| JP | 2006289075 A | 10/2006 |
| JP | 2007181714 | 7/2007 |
| WO | WO 00/07525 A1 | 2/2000 |
| WO | WO 00/64389 A1 | 11/2000 |
| WO | WO 00/64393 A1 | 11/2000 |
| WO | WO 01/97727 A1 | 12/2001 |
| WO | WO 02/36052 A1 | 5/2002 |
| WO | WO 02/074052 A2 | 9/2002 |
| WO | WO 02/080811 A2 | 10/2002 |
| WO | WO 03/015659 A2 | 2/2003 |
| WO | WO 03/045290 A1 | 6/2003 |
| WO | WO 2004/054643 A1 | 7/2004 |
| WO | WO 2004/093761 A1 | 11/2004 |
| WO | WO 2005/105197 A2 | 11/2005 |
| WO | WO 2006/066103 A2 | 6/2006 |
| WO | WO 2007/035356 A2 | 3/2007 |
| WO | WO 2007/047744 A2 | 4/2007 |
| WO | WO 2007/087061 A2 | 8/2007 |
| WO | WO 2008/002377 A1 | 1/2008 |
| WO | WO 2008/005873 A2 | 1/2008 |
| WO | WO 2009/120960 A2 | 10/2009 |
| WO | WO 2011/053512 A1 | 5/2011 |
| WO | WO 2011/057283 A1 | 5/2011 |

OTHER PUBLICATIONS

D'Ermo, et al.; Our results with the operation of ab externo trabeculotomy; Ophthalmologica; vol. 163; pp. 347-355; Feb. 1971.

Ellingsen et al.; Trabeculotomy and sinusotomy in enucleated human eyes; Investigative Ophthalmology; vol. 11; pp. 21-28; Jan. 1972.

Grant; Experimental aqueous perfusion in enucleated human eyes; Archives of Ophthalmology; vol. 69; pp. 783-801; Jun. 1963.

Johnstone et al.; "Microsurgery of Schlemm's Canal and the Human Aqueous Outflow System;" American Journal of Ophthalmology, vol. 76 (6): 906-917; Dec. 1973.

Lee et al.; Aqueous-venous shunt and intraocular pressure. Preliminary report of animal studies; Investigative Ophthalmology; vol. 5; No. 1; pp. 59-64; Feb. 1966.

Moses, Robert; The effect of intraocular pressure on resistance to outflow; Survey of Ophthalmology; vol. 22; No. 2; pp. 88-100; Sep.-Oct. 1977.

Mäepea et al.; The pressures in the episcleral veins, schlemm's canal and the trabecular meshwork in monkeys: effects of changes in intraocular pressure; Exp. Eye Res.; vol. 49; pp. 645-663; Oct. 1989.

(56) References Cited

OTHER PUBLICATIONS

Rosenquist et al.; Outflow resistance of enucleated human eyes at two different perfusion pressures and different extents of trabeculotomy; Current Eye Res.; vol. 8; No. 12; pp. 1233-1240; Dec. 1989.

Savage, James; Gonioscopy in the management of glaucoma; Am. Academy of Ophthalmology; Focal Points; vol. XXIV; No. 3; pp. 1-14; Mar. 2006.

Schultz, Jared; Canaloplasty procedure shows promise for open-angle glaucoma in European study; Ocular Surgery News; vol. 34; Mar. 1, 2007.

Smit et al.; Effects of viscoelastic injection into schlemm's canal in primate and human eyes; J. Am. Academy of Ophthalmology; vol. 109; No. 4; pp. 786-792; Apr. 2002.

Spiegel et al.; Schlemm's canal implant: a new method to lower intraocular pressure in patients with POAG?; Ophthalmic Surgery and Lasers; vol. 30; No. 6; pp. 492-494; Jun. 1999.

Lynch, Mary G.; U.S. Appl. No. 60/131,030 entitled "Devices and methods for treating glaucoma by enhancing aqueous outflow through schlemm's canal and anterior chamber angle ," filed Apr. 26, 1999.

Euteneuer et al.; U.S. Appl. No. 13/968,051 entitled "Methods and Apparatus for Treating Glaucoma," filed Aug. 15, 2013.

Wardle et al.; U.S. Appl. No. 14/139,403 entitled "Ocular implants for delivery into the eye," filed Dec. 23, 2013.

* cited by examiner

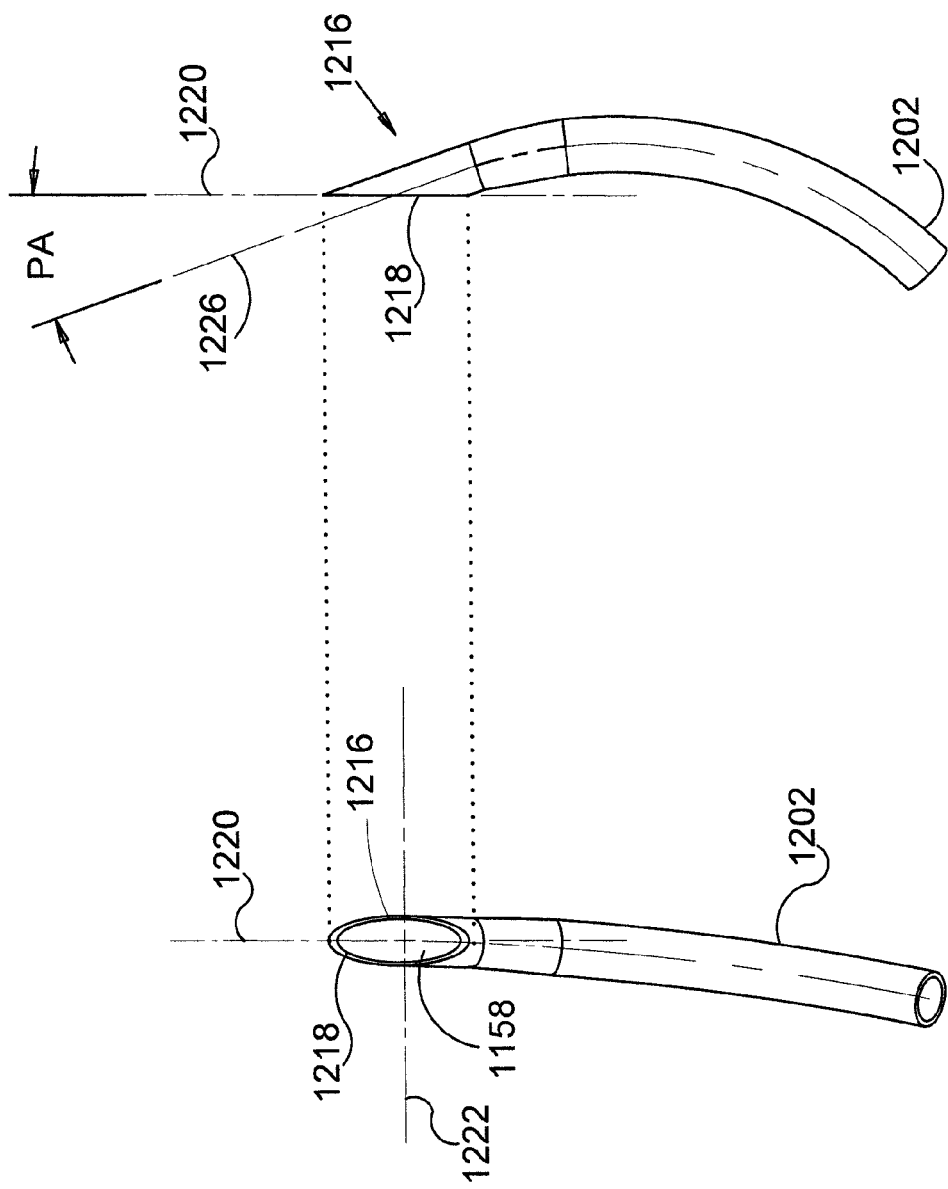

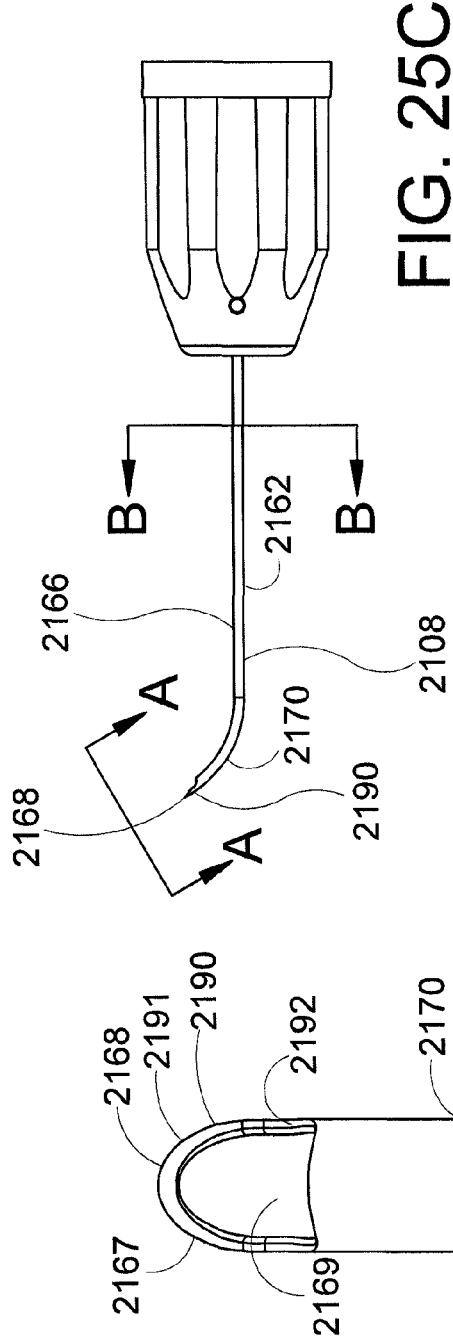
FIG. 25C
FIG. 25B
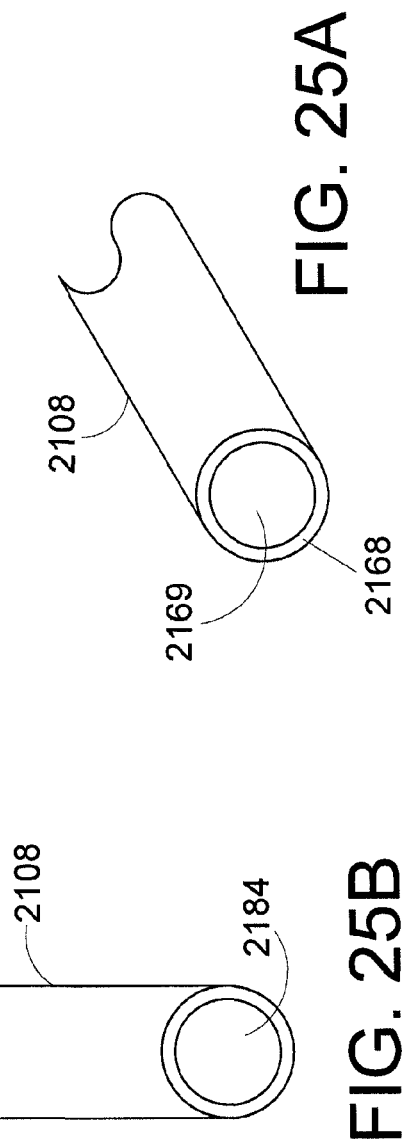
FIG. 25A

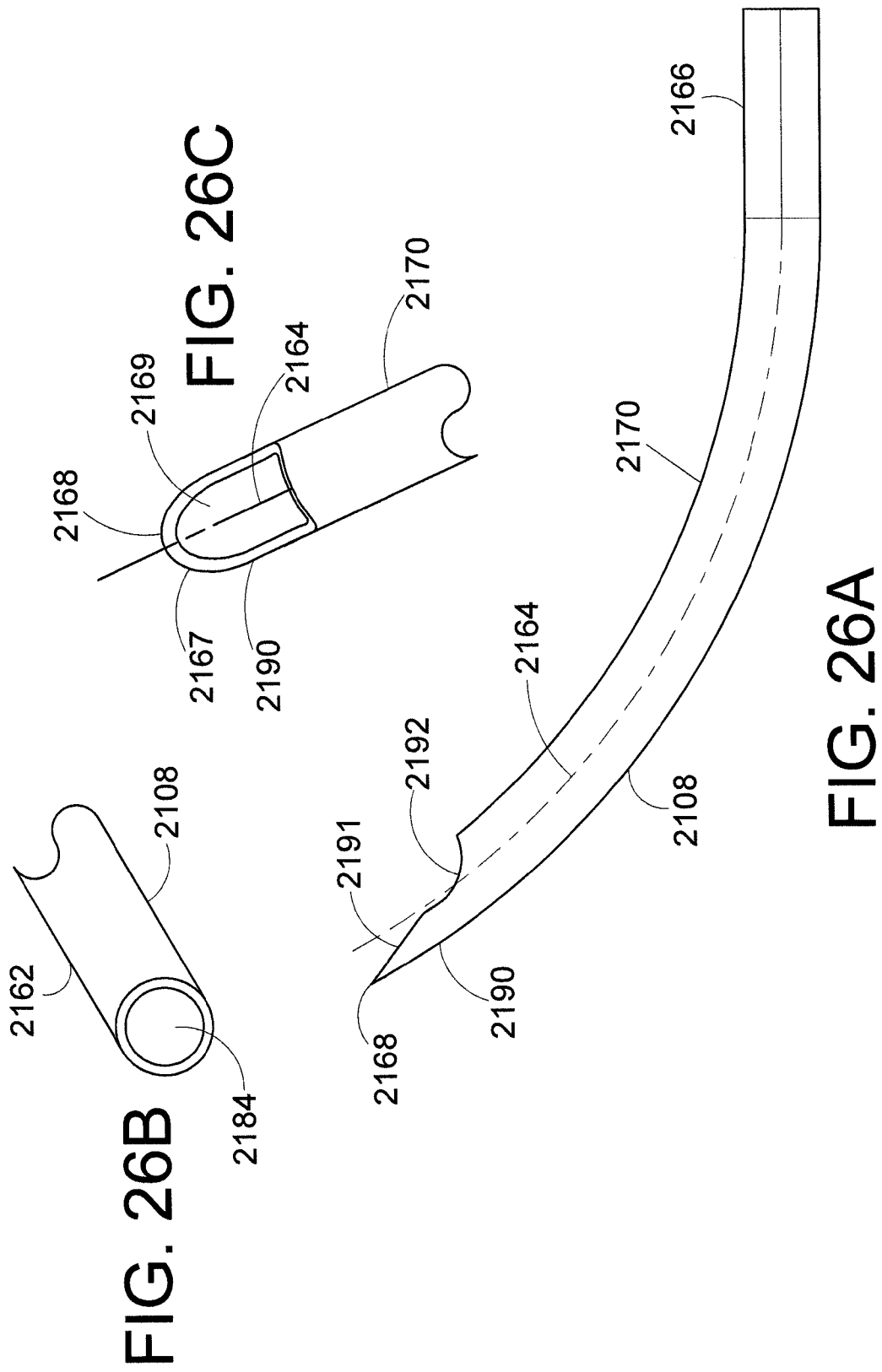

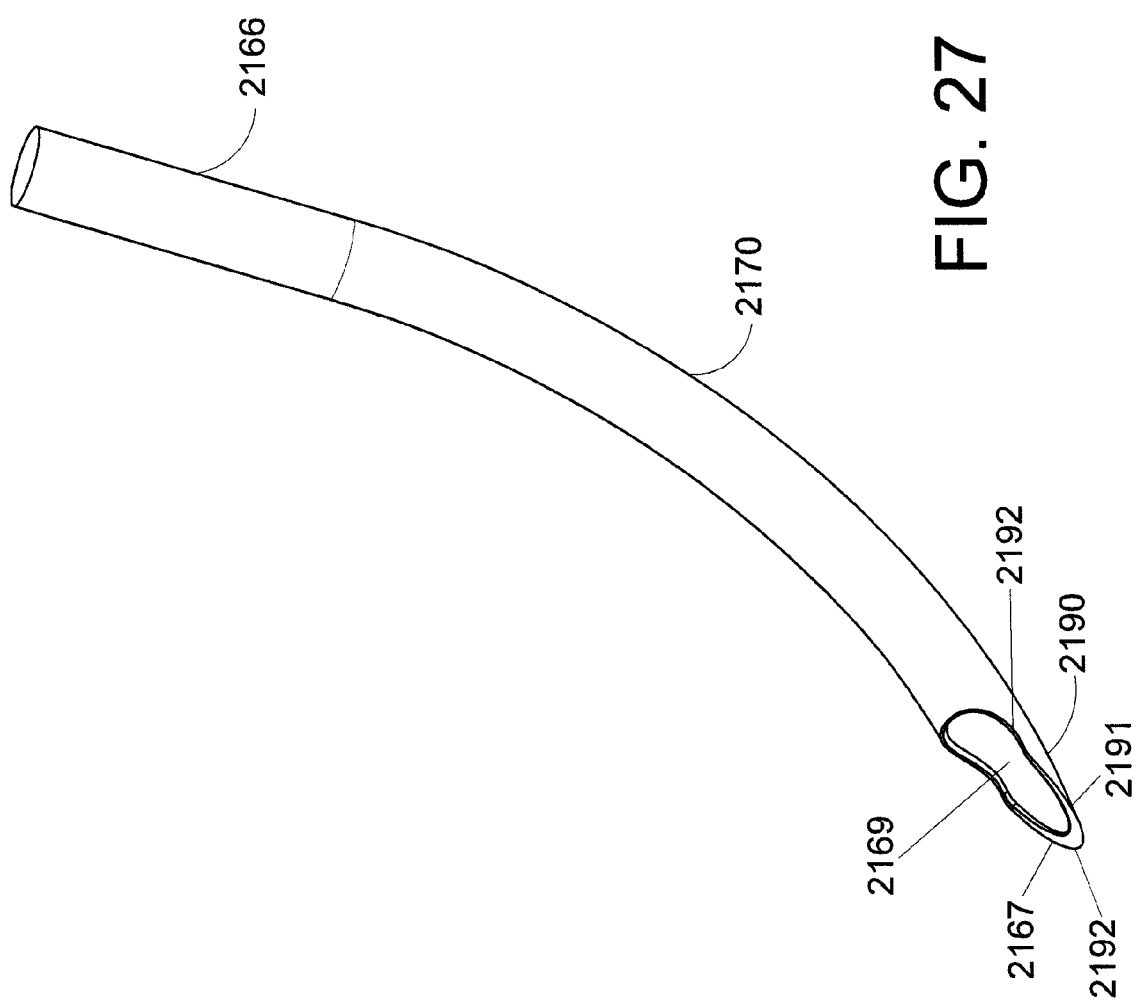

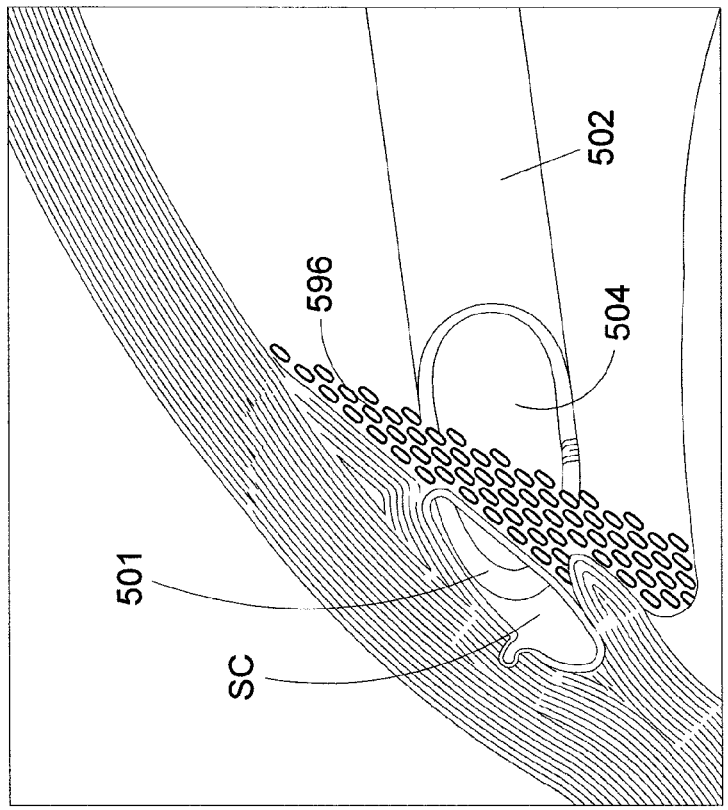
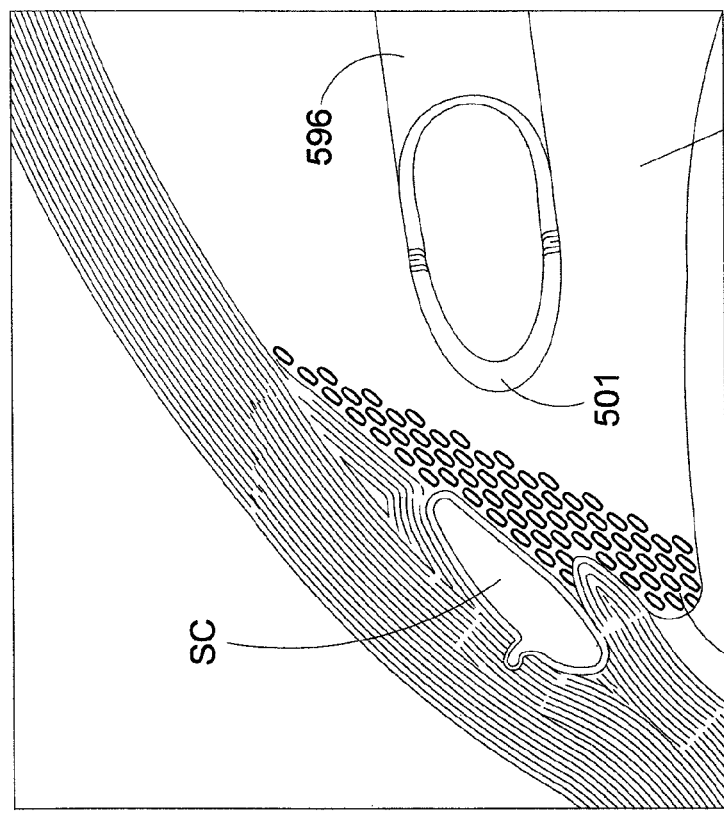

METHODS AND APPARATUS FOR DELIVERING OCULAR IMPLANTS INTO THE EYE

CROSS REFERENCE TO RELATED APPLICATIONS

This application is a continuation of U.S. application Ser. No. 13/681,365, filed Nov. 19, 2012, now U.S. Pat. No. 8,551,166, which application is a divisional of U.S. application Ser. No. 12/632,738, filed Dec. 7, 2009, now U.S. Pat. No. 8,337,509, which application claims the benefit of the following: U.S. Provisional Application No. 61/120,222, filed Dec. 5, 2008; U.S. Provisional Application No. 61/120,295, filed Dec. 5, 2008; U.S. Provisional Application No. 61/224,156, filed Jul. 9, 2009; and U.S. Provisional Application No. 61/224,158, filed Jul. 9, 2009. Said U.S. application Ser. No. 12/632,738, a continuation-in-part of U.S. application Ser. No. 11/943,289, filed Nov. 20, 2007, now U.S. Pat. No. 8,512,404. All of these applications are incorporated by reference as if fully set forth herein.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The present invention relates generally to devices that are implanted within the eye. More particularly, the present invention relates to systems, devices and methods for delivering ocular implants into the eye.

BACKGROUND OF THE INVENTION

According to a draft report by The National Eye Institute (NEI) at The United States National Institutes of Health (NIH), glaucoma is now the leading cause of irreversible blindness worldwide and the second leading cause of blindness, behind cataract, in the world. Thus, the NEI draft report concludes, "it is critical that significant emphasis and resources continue to be devoted to determining the pathophysiology and management of this disease." Glaucoma researchers have found a strong correlation between high intraocular pressure and glaucoma. For this reason, eye care professionals routinely screen patients for glaucoma by measuring intraocular pressure using a device known as a tonometer. Many modern tonometers make this measurement by blowing a sudden puff of air against the outer surface of the eye.

The eye can be conceptualized as a ball filled with fluid. There are two types of fluid inside the eye. The cavity behind the lens is filled with a viscous fluid known as vitreous humor. The cavities in front of the lens are filled with a fluid know as aqueous humor. Whenever a person views an object, he or she is viewing that object through both the vitreous humor and the aqueous humor.

Whenever a person views an object, he or she is also viewing that object through the cornea and the lens of the eye. In order to be transparent, the cornea and the lens can include no blood vessels. Accordingly, no blood flows through the cornea and the lens to provide nutrition to these tissues and to remove wastes from these tissues. Instead, these functions are performed by the aqueous humor. A continuous flow of aqueous humor through the eye provides nutrition to portions of the eye (e.g., the cornea and the lens) that have no blood vessels. This flow of aqueous humor also removes waste from these tissues.

Aqueous humor is produced by an organ known as the ciliary body. The ciliary body includes epithelial cells that continuously secrete aqueous humor. In a healthy eye, a stream of aqueous humor flows out of the anterior chamber of the eye through the trabecular meshwork and into Schlemm's canal as new aqueous humor is secreted by the epithelial cells of the ciliary body. This excess aqueous humor enters the venous blood stream from Schlemm's canal and is carried along with the venous blood leaving the eye.

When the natural drainage mechanisms of the eye stop functioning properly, the pressure inside the eye begins to rise. Researchers have theorized prolonged exposure to high intraocular pressure causes damage to the optic nerve that transmits sensory information from the eye to the brain. This damage to the optic nerve results in loss of peripheral vision. As glaucoma progresses, more and more of the visual field is lost until the patient is completely blind.

In addition to drug treatments, a variety of surgical treatments for glaucoma have been performed. For example, shunts were implanted to direct aqueous humor from the anterior chamber to the extraocular vein (Lee and Scheppens, "Aqueous-venous shunt and intraocular pressure," *Investigative Ophthalmology* (February 1966)). Other early glaucoma treatment implants led from the anterior chamber to a subconjunctival bleb (e.g., U.S. Pat. No. 4,968,296 and U.S. Pat. No. 5,180,362). Still others were shunts leading from the anterior chamber to a point just inside Schlemm's canal (Spiegel et al., "Schlemm's canal implant: a new method to lower intraocular pressure in patients with POAG?" *Ophthalmic Surgery and Lasers* (June 1999); U.S. Pat. No. 6,450,984; U.S. Pat. No. 6,450,984).

SUMMARY OF THE INVENTION

The invention pertains to aspects of ocular implants and ocular implant delivery systems. One aspect of the invention provides a cannula for an ocular implant delivery system. In some embodiments, the cannula includes a tubular member having a curved portion, a distal opening surrounded by a distal opening surface, and a distal tip, the distal tip being adapted to be inserted into an anterior chamber of a human subject's eye, through trabecular meshwork and into Schlemm's canal of the eye, a proximal portion of the tubular member being adapted to extend from a location exterior to the eye when the distal tip is in Schlemm's canal of the eye, the cannula being further adapted to cooperate with an advancement mechanism to advance an ocular implant through the tubular member toward and through the distal opening into Schlemm's canal of the eye when the distal tip is disposed in Schlemm's canal.

In some embodiments, the cannula's tubular member also has a tongue region extending proximally from the distal tip on one side of the tubular member, with the tongue region forming at least part of the distal opening surface. In some embodiments the distal opening surface extends solely proximally from the distal tip, and the distal opening surface may be disposed in a distal opening plane. The tubular member curved portion may also define a curve plane, and the distal opening plane may be at an angle other than 90 degrees with respect to the curve plane.

In some embodiments of the cannula, the distal opening surface has a first section disposed in a distal opening plane disposed at a first section angle between 0 degrees and 90 degrees with respect to a longitudinal axis of the tubular member at the distal opening and a second section whose angle with respect to the longitudinal axis of the tubular member varies from an angle less than the first section angle at a distal limit of the second section to an angle greater than the first section angle at a proximal limit of the second section.

In other embodiments of the cannula, the distal opening surface has an edge formed from a circumferential portion of a cylindrical envelope defined by the tubular member, the angular extent of the circumferential portion within the cylindrical envelope increasing from the distal tip proximally to a first point, the angular extent of the circumferential portion within the cylindrical envelope decreasing between the first point and a second point proximal to the first point, the angular extent of the circumferential portion within the cylindrical envelope increasing to 360 degrees between the second point and a third point proximal to the second point.

In some embodiments of the cannula, the tubular member also has a second tongue region and a stop member defining the distal opening surface.

In some embodiments, an external diameter of the tubular member at a distal end of the tubular member is less than an external diameter of the tubular member proximal to the distal opening. The curved portion of the tubular member may also have a bend angle between 105 degrees and 165 degrees.

Another aspect of the invention provides an ocular implant system including an ocular implant having an inlet sized and configured to be disposed in an anterior chamber of a human subject's eye and a body sized and configured to be disposed in Schlemm's canal of the eye, the ocular implant being adapted to bend preferentially in a preferential bending plane; and a delivery cannula comprising a tubular member with a curved portion, a distal opening surrounded by a distal opening surface, and a distal tip, the distal tip being adapted to be inserted into an anterior chamber of a human subject's eye, through trabecular meshwork and into Schlemm's canal of the eye, the tubular member being adapted to extend from a location exterior to the eye when the distal tip is in Schlemm's canal of the eye, the cannula being further adapted to cooperate with an advancement mechanism to advance the ocular implant through at least the curved portion of the tubular member toward and through the distal opening into Schlemm's canal of the eye when the distal tip of the delivery tool is disposed in Schlemm's canal.

In some embodiments of the ocular implant system, a central axis of the cannula defines a cannula curvature plane, the ocular implant being oriented within the cannula so that the implant preferential bending plane is co-planar with the cannula curvature plane.

Yet another aspect of the invention provides a method of deploying an ocular implant into Schlemm's canal of a human eye. The method may include the following steps: inserting a distal tip of a delivery tool within an anterior chamber of the eye through trabecular meshwork of the eye into Schlemm's canal of the eye; and advancing an ocular implant through a curved portion and a distal opening of the delivery tool to place a body portion of the ocular implant in Schlemm's canal and an inlet portion of the ocular implant in the anterior chamber.

In some embodiments, the delivery tool has a curved distal portion, the inserting step including the step of aligning the curved distal portion with respect to Schlemm's canal so that the ocular implant is delivered into the center of Schlemm's canal or slightly radially inward of an outer wall of Schlemm's canal. The curved distal portion of the delivery tool may have a radius of curvature smaller than that of Schlemm's canal.

In some embodiments, the inserting step includes the step of advancing the distal tip into Schlemm's canal until a stop portion of a distal opening surface surrounding the distal opening engages the trabecular meshwork. The inserting step may also include the step of depressing trabecular meshwork and Schlemm's canal tissue with the distal tip with a distal opening surface surrounding the distal opening, the distal opening surface being disposed at an angle other than 90 degrees with respect to a longitudinal axis of the delivery tool.

In embodiments in which the delivery tool has a distal opening surface surrounding the distal opening, the inserting step may include the step of inserting less than all of the distal opening surface into Schlemm's canal.

In some embodiments, the delivery tool has a distal opening surface surrounding the distal opening and the distal tip is disposed at the distal end of a tongue. In such embodiments the inserting step may include the step of inserting the tongue into Schlemm's canal. The advancing step may also include the step of advancing the ocular implant through the distal opening while a portion of the distal opening surface is disposed in Schlemm's canal and a portion of the distal opening surface is disposed outside of Schlemm's canal.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 17A and 17B are plan views further illustrating the tubular member of the cannula assembly shown in FIG. 12.

FIG. 25C is a plan view showing a cannula. FIG. 25B is a cross sectional view of the cannula sectioned along cutting line B-B shown in FIG. 25C. FIG. 25A is an axial plan view created from the viewpoint illustrated by line A-A in FIG. 25C.

FIGS. 26A, 26B, and 26C are three orthographic views of illustrating the structural features of an exemplary ocular implant delivery system cannula.

FIG. 27 is an isometric view of the ocular implant delivery system cannula illustrating a tongue of the cannula.

FIGS. 36A and 36B are partial section and perspective views illustrating insertion of the distal tip of an ocular implant delivery system cannula into Schlemm's canal.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 1:
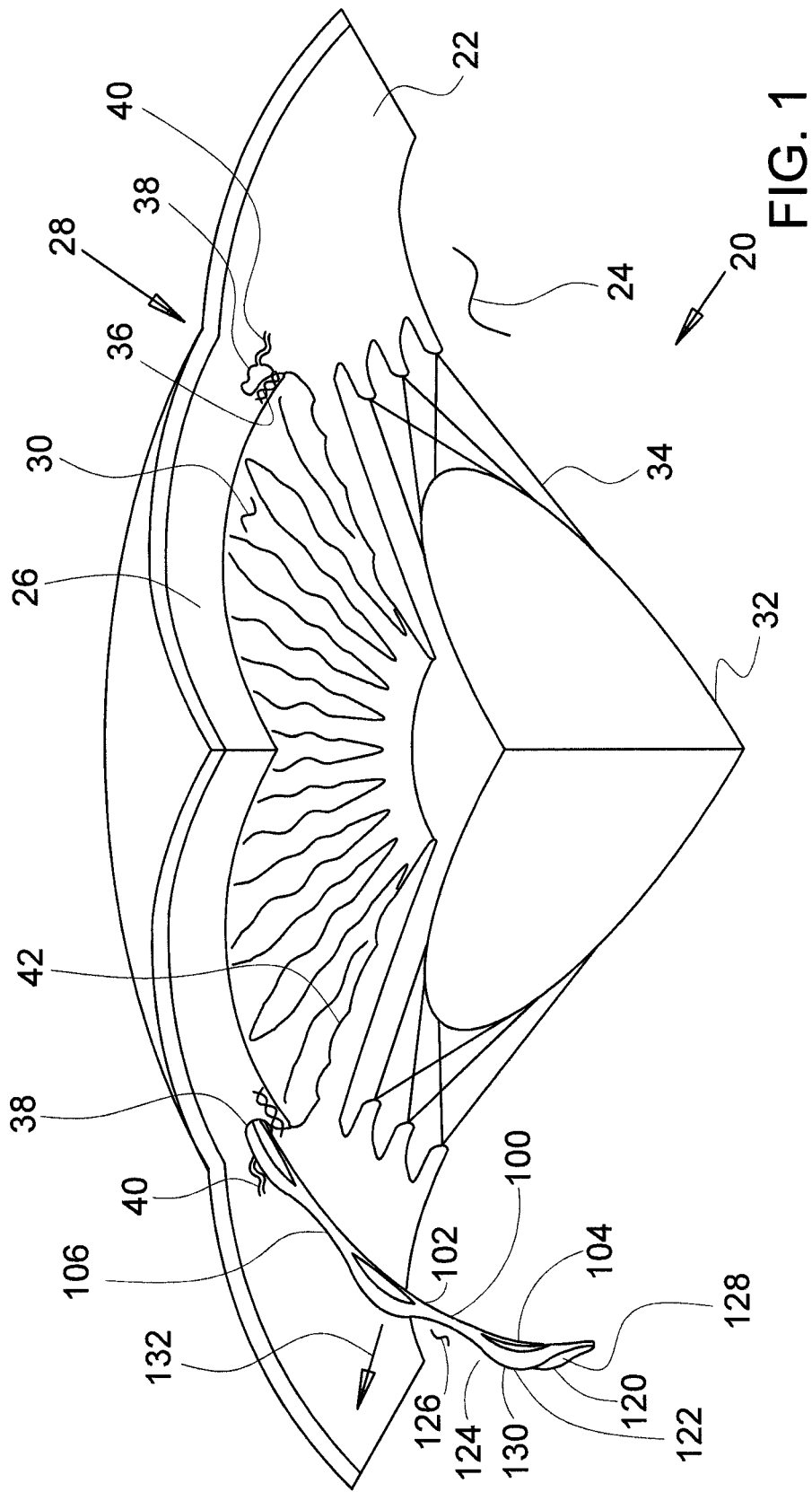
FIG. 1 is a stylized perspective view depicting an exemplary ocular implant extending from a portion of a human eye.

Apparatus and methods in accordance with the present detailed description may be used to deliver an ocular implant into a subject's eye and to place distal portion of an ocular implant in Schlemm's canal of an eye. FIG. 1 is a stylized perspective view depicting a portion of a human eye 20. Eye 20 can be conceptualized as a fluid filled ball having two chambers. Sclera 22 of eye 20 surrounds a posterior chamber 24 filled with a viscous fluid known as vitreous humor. Cornea 26 of eye 20 encloses an anterior chamber 30 that is filled with a fluid know as aqueous humor. The cornea 26 meets the sclera 22 at a limbus 28 of eye 20. A lens 32 of eye 20 is located between anterior chamber 30 and posterior chamber 24. Lens 32 is held in place by a number of ciliary zonules 34.

Whenever a person views an object, he or she is viewing that object through the cornea, the aqueous humor, and the lens of the eye. In order to be transparent, the cornea and the lens can include no blood vessels. Accordingly, no blood flows through the cornea and the lens to provide nutrition to these tissues and to remove wastes from these tissues. Instead, these functions are performed by the aqueous humor. A continuous flow of aqueous humor through the eye provides nutrition to portions of the eye (e.g., the cornea and the lens) that have no blood vessels. This flow of aqueous humor also removes waste from these tissues.

Aqueous humor is produced by an organ known as the ciliary body. The ciliary body includes epithelial cells that continuously secrete aqueous humor. In a healthy eye, a stream of aqueous humor flows out of the eye as new aqueous humor is secreted by the epithelial cells of the ciliary body. This excess aqueous humor enters the blood stream and is carried away by venous blood leaving the eye.

In a healthy eye, aqueous humor flows out of the anterior chamber 30 through the trabecular meshwork 36 and into Schlemm's canal 38, located at the outer edge of the iris 42. Aqueous humor exits Schlemm's canal 38 by flowing through a number of outlets 40. After leaving Schlemm's canal 38, aqueous humor is absorbed into the venous blood stream.

In FIG. 1, an ocular implant 100 is disposed in Schlemm's canal 38 of eye 20. Ocular implant 100 has a body 102 including a plurality of tissue supporting frames 104 and a plurality of spines 106. Body 102 also includes a first edge 120 and a second edge 122 that define a first opening 124. First opening 124 is formed as a slot and fluidly communicates with an elongate channel 126 defined by an inner surface 128 of body 102. With reference to FIG. 1, it will be appreciated that first opening 124 is disposed on an outer side 130 of body 102. Accordingly, channel 126 opens in a radially outward direction 132 via first opening 124.

Ocular implant 100 may be inserted into Schlemm's canal of a human eye to facilitate the flow of aqueous humor out of the anterior chamber. This flow may include axial flow along Schlemm's canal, flow from the anterior chamber into Schlemm's canal, and flow leaving Schlemm's canal via outlets communicating with Schlemm's canal. When in place within the eye, ocular implant 100 will support trabecular mesh tissue and Schlemm's canal tissue and will provide for improved communication between the anterior chamber and Schlemm's canal (via the trabecular meshwork) and between pockets or compartments along Schlemm's canal. As shown in FIG. 1, the implant is preferably oriented so that the first opening 124 is disposed radially outwardly within Schlemm's canal.

Figure 2:
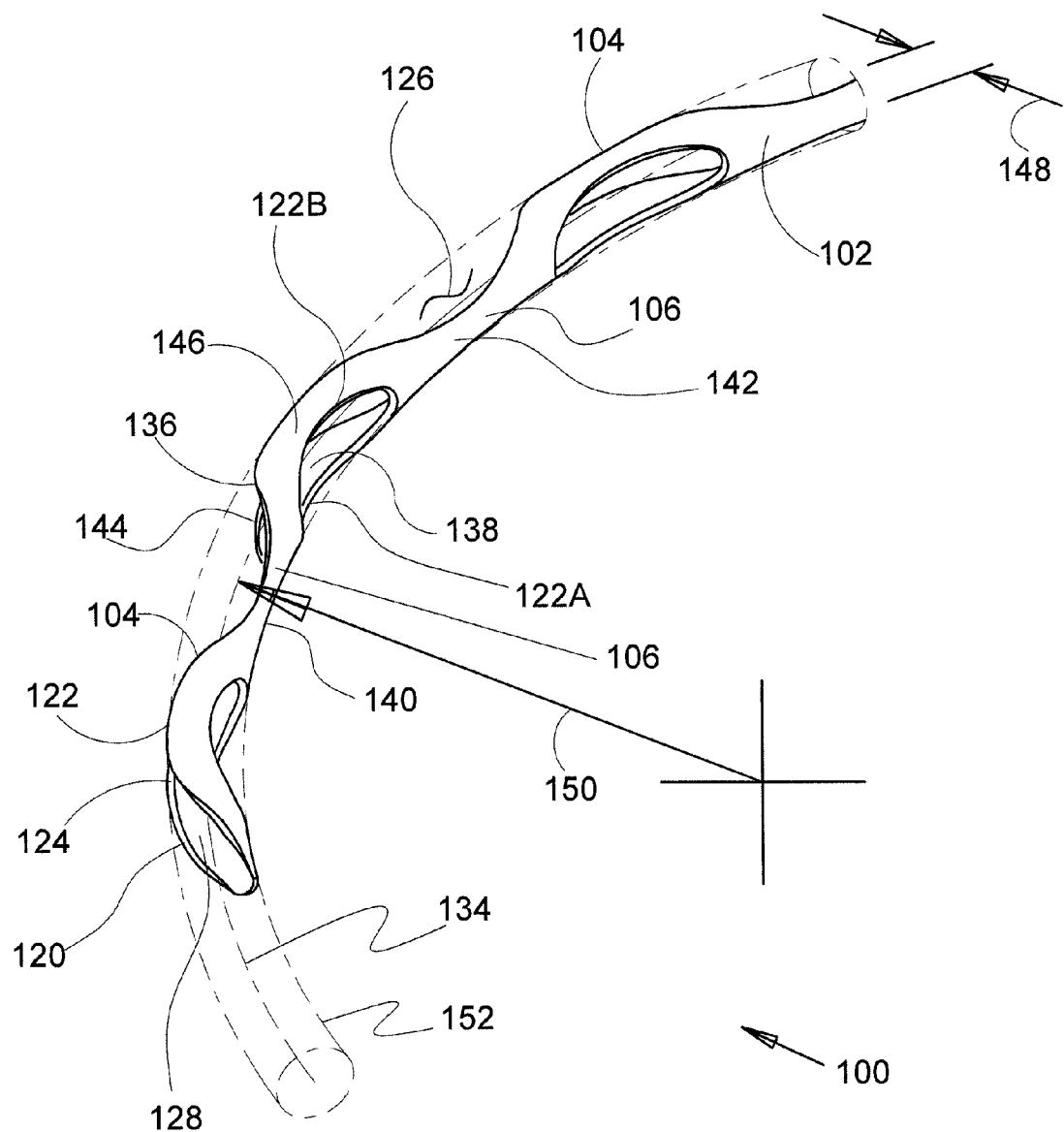
FIG. 2 is a perspective view showing a portion of the ocular implant shown in FIG. 1.

FIG. 2 is an enlarged perspective view showing a portion of ocular implant 100 shown in the previous figure. Ocular implant 100 has a body 102 that extends along a generally curved longitudinal axis 134. Body 102 has a plurality of tissue supporting frames 104 and a plurality of spines 106. As shown in FIG. 2, these spines 106 and frames 104 are arranged in a repeating AB pattern in which each A is a tissue supporting frame and each B is a spine. In the embodiment of FIG. 2, one spine extends between each adjacent pair of frames 104.

For example, frame 136 of ocular implant 100 is disposed between a first spine 140 and a second spine 142. Frame 136 is formed as a first strut 144 that extends between first spine 140 and second spine 142 and a second strut 146 extending between first spine 140 and second spine 142. In the exemplary embodiment of FIG. 2, struts 144 and 146 each undulates in a circumferential direction as it extends longitudinally between first spine 140 and second spine 142.

In the embodiment of FIG. 2, body 102 has a longitudinal radius of curvature 150 and a lateral radius of curvature 148. Body 102 of ocular implant 100 includes a first edge 120 and a second edge 122 that define first opening 124. First opening 124 fluidly communicates with an elongate channel 126 defined by an inner surface 128 of body 102. A second opening 138 is defined by a second edge 122A of first strut 144 and a second edge 122B of second strut 146. First opening 124, second opening 138 and additional openings defined by ocular implant 100 allow aqueous humor to flow laterally across and/or laterally through ocular implant 100. The outer surfaces of body 102 define a volume 152.

Figure 3:
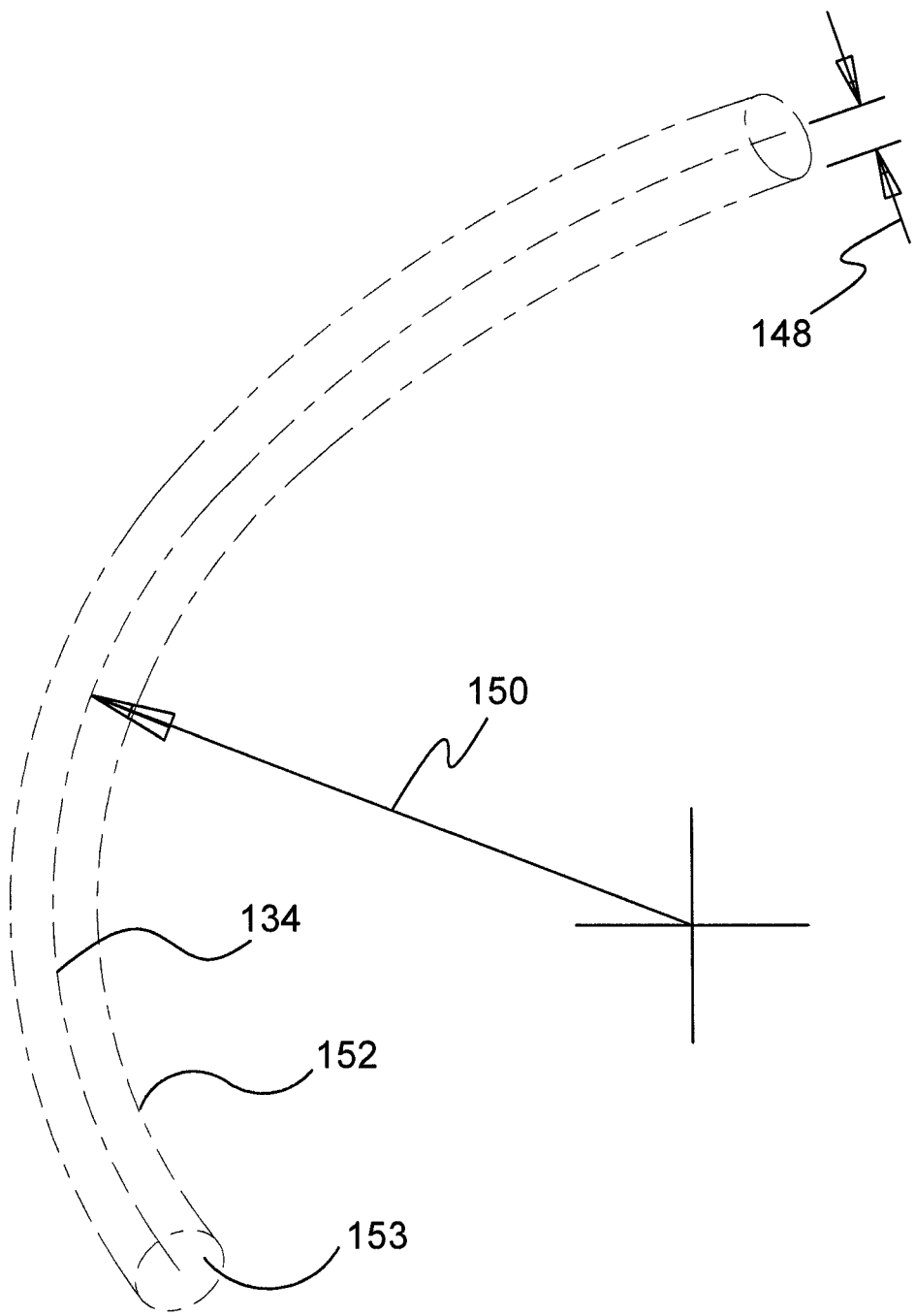
FIG. 3 is a perspective view illustrating a volume defined by the body of the ocular implant shown in FIG. 2.

FIG. 3 is an additional perspective view showing volume 152 defined by the body of the ocular implant shown in the previous figure. With reference to FIG. 3, it will be appreciated that volume 152 extends along a generally curved longitudinal axis 134. Volume 152 has a longitudinal radius 150, a lateral radius 148, and a generally circular lateral cross section 153.

Figure 4:
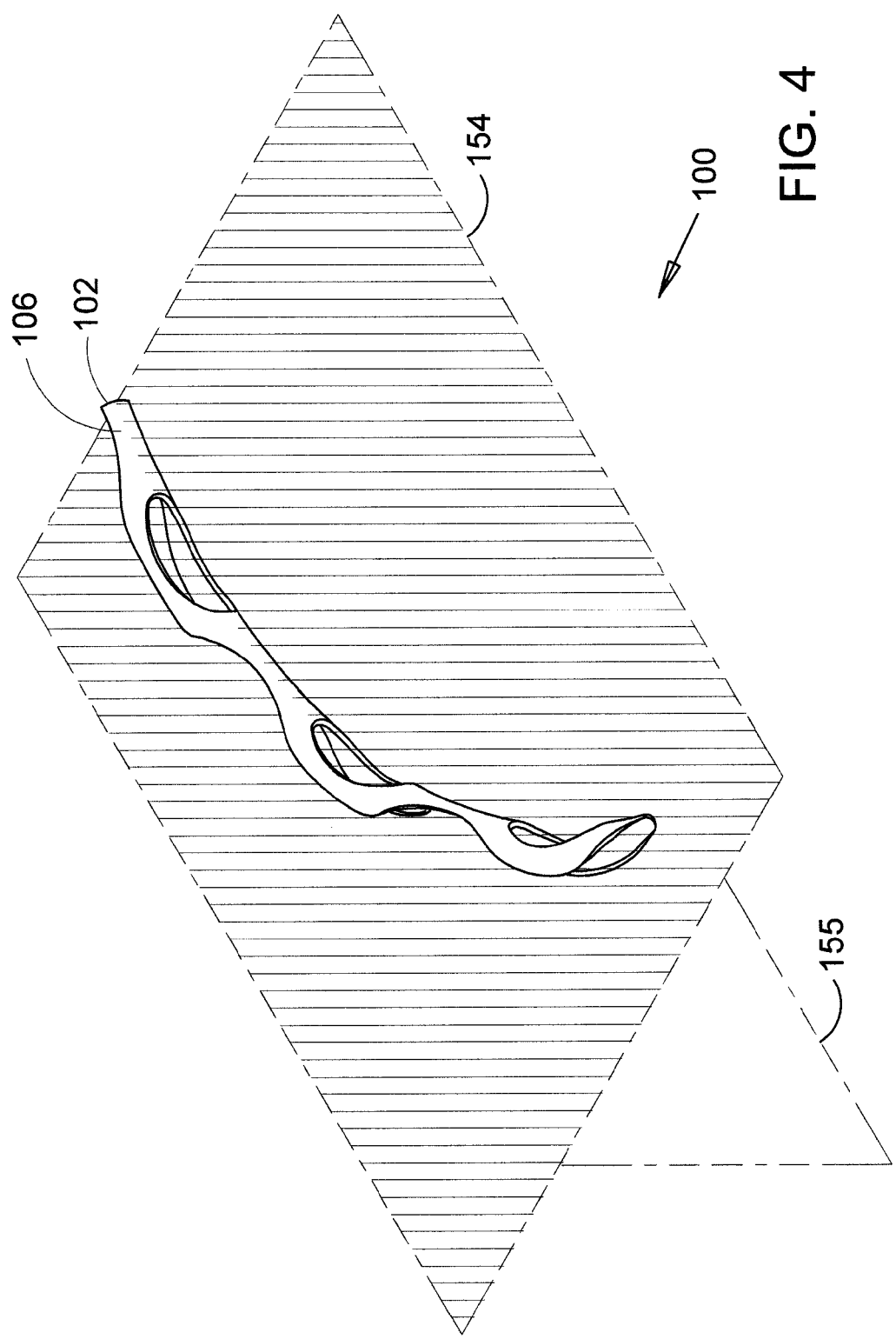
FIG. 4 is a perspective view illustrating a first plane and a second plane that both intersect an exemplary ocular implant.

FIG. 4 is a perspective view showing a first plane 154 and a second plane 155 that both intersect ocular implant 100. In FIG. 4, first plane 154 is delineated with hatch marks. With reference to FIG. 4, it will be appreciated that spines 106 of body 102 are generally aligned with one another and that first plane 154 intersects all spines 106 shown in FIG. 4. In the embodiment of FIG. 4, body 102 of ocular implant 100 is generally symmetric about first plane 154.

In the embodiment of FIG. 4, the flexibility of body 102 is at a maximum when body 102 is bending along first plane 154, and body 102 has less flexibility when bending along a plane other than first plane 154 (e.g., a plane that intersects first plane 154). Accordingly, first plane 154 may be generally referred to as a plane of preferential bending. In the embodiment shown in FIG. 4, for example, body 102 has a second flexibility when bending along second plane 155 that is less than the first flexibility that body 102 has when bending along first plane 154.

Stated another way, in the embodiment of FIG. 4, the bending modulus of body 102 is at a minimum when body 102 is bent along first plane 154. Body 102 has a first bending modulus when bent along first plane 154 and a greater bending modulus when bent along a plane other than first plane 154 (e.g., a plane that intersects first plane 154). For example, in the embodiment shown in FIG. 4, body 102 has a second bending modulus when bent along second plane 155 that is greater than the first bending modulus that body 102 has when bent along first plane 154.

Figure 5:
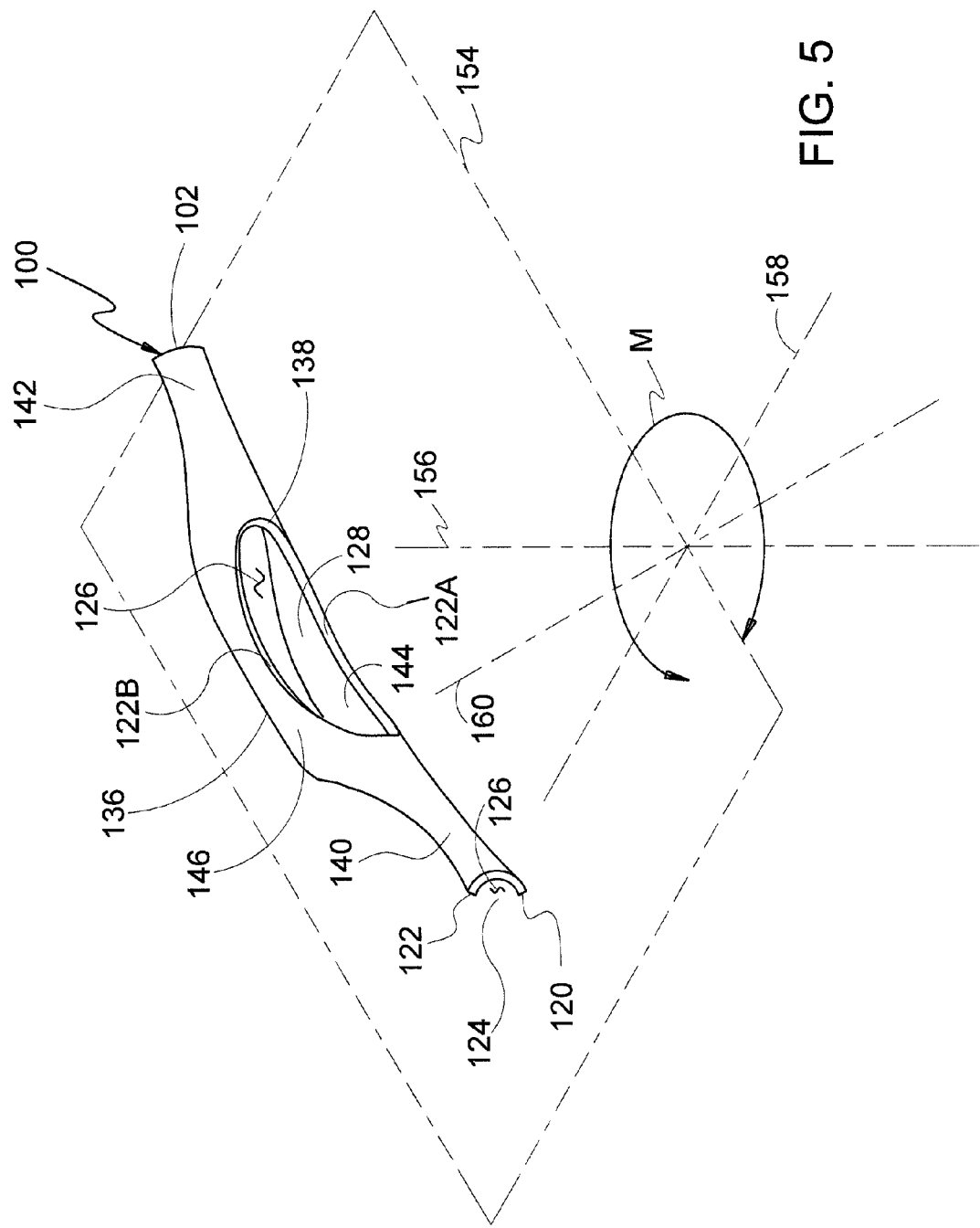
FIG. 5 is an enlarged perspective view showing a portion of the ocular implant shown in FIG. 4.

FIG. 5 is an enlarged perspective view showing a portion of ocular implant 100 shown in the previous figure. In the exemplary embodiment of FIG. 5, a bending moment M is being applied to body 102 of ocular implant 100. Bending moment M acts about a first axis 156 that is generally orthogonal to first plane 154. A second axis 158 and a third axis 160 are also shown in FIG. 5. Second axis 158 is generally perpendicular to first axis 156. Third axis 160 is skewed relative to first axis 156.

In the embodiment of FIG. 5, the flexibility of body 102 is at a maximum when body 102 is bent by a moment acting about first axis 156, and body 102 has less flexibility when bent by a moment acting about an axis other than first axis 156 (e.g., second axis 158 and third axis 160). Stated another way, the bending modulus of body 102 is at a minimum when body 102 is bent by a moment acting about first axis 156, and body 102 has a greater bending modulus when bent by a moment acting about an axis other than first axis 156 (e.g., second axis 158 and third axis 160).

Figure 6:
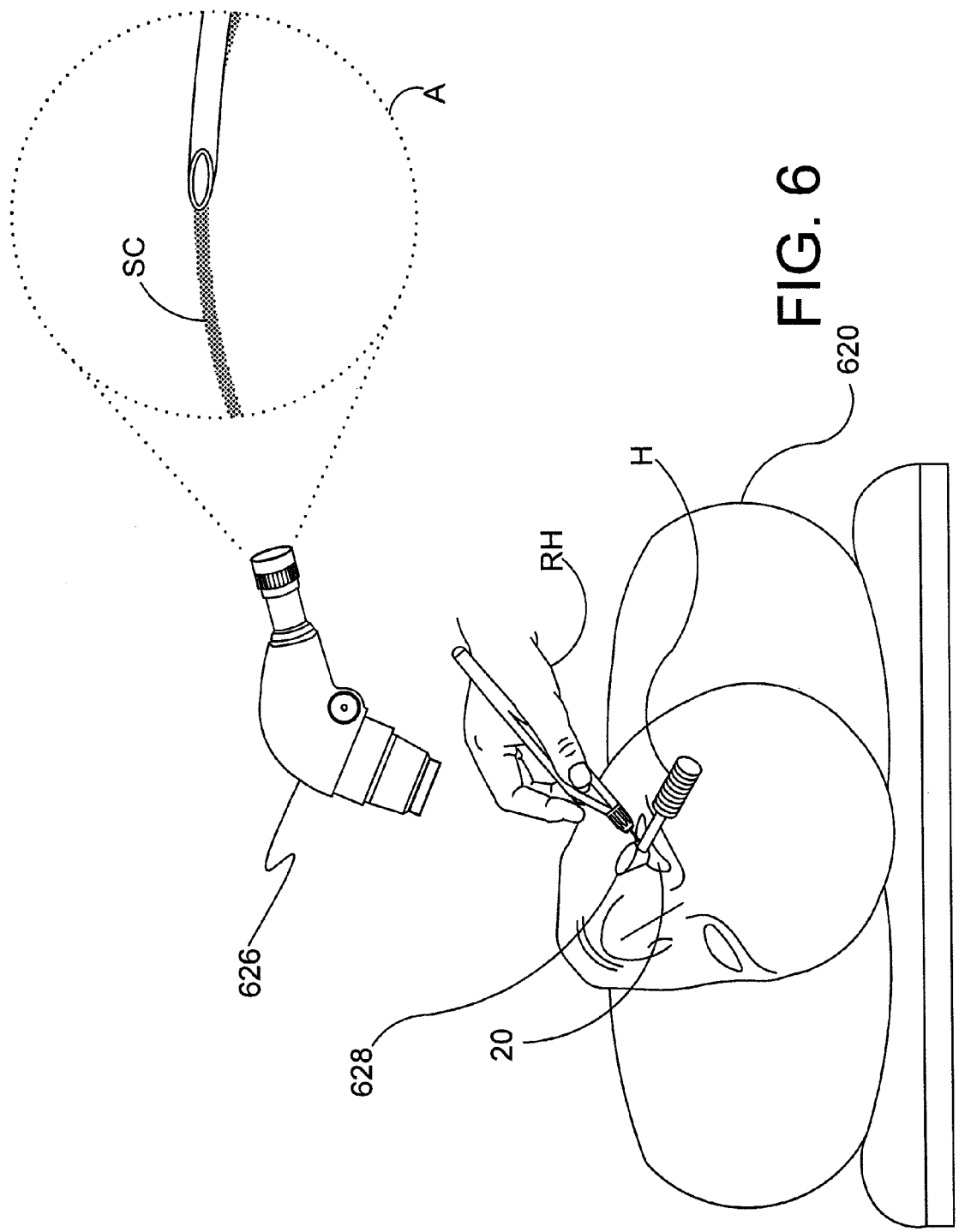
FIG. 6 is stylized representation of an exemplary medical procedure in accordance with the present disclosure.

FIG. 6 is a stylized representation of an exemplary medical procedure in accordance with this detailed description. In the exemplary procedure of FIG. 6, a physician is treating an eye 20 of a patient 620. In the exemplary procedure of FIG. 6, a physician is holding a delivery system in his or her right hand RH. The physician's left hand (not shown) may be used to hold the handle H of a gonio lens 628. It will be appreciated that some physicians may prefer holding the delivery system handle in the left hand and the gonio lens handle H in the right hand RH.

During the exemplary procedure illustrated in FIG. 6, the physician may view the interior of the anterior chamber using a microscope 626 and gonio lens 628. Detail A of FIG. 6 is a stylized simulation of the image viewed by the physician. A distal portion of a cannula is visible in Detail A. The distal end of the cannula is positioned near Schlemm's canal SC of eye 22. A shadow-like line indicates the location of Schlemm's canal SC which is lying under various tissue (e.g., the trabecular meshwork) that surround the anterior chamber.

Figure 7:
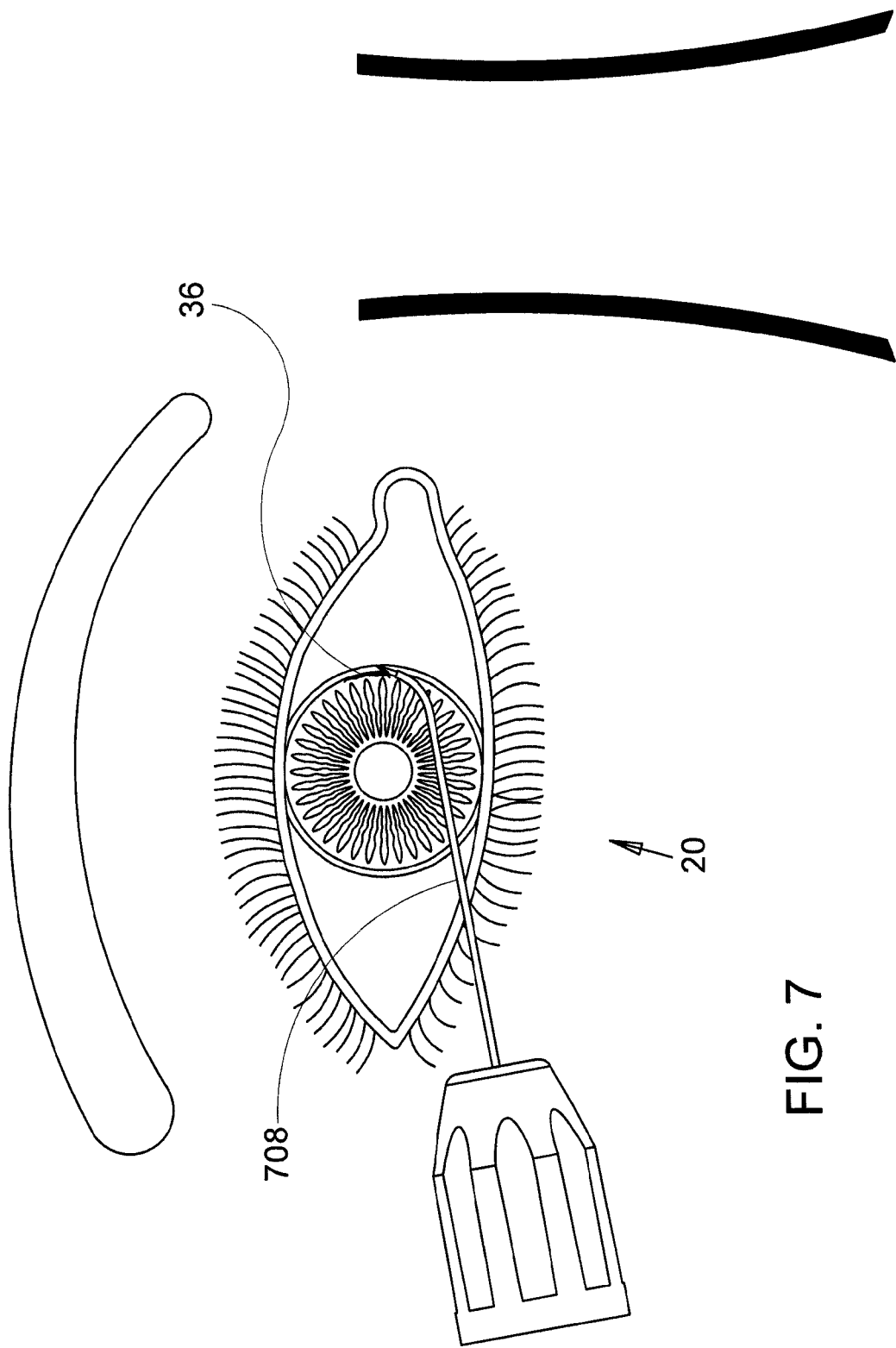
FIG. 7 is an enlarged plan view showing illustrating insertion of an ocular implant delivery system cannula into the eye shown in the previous figure.

FIG. 7 is an enlarged plan view showing a portion of the face shown in the previous figure. In the embodiment of FIG. 7, cannula 708 extends through a cornea of eye 20 so that the distal end of cannula 708 is disposed in the anterior chamber of eye 20. With reference to FIG. 7, it will be appreciated that the distal tip of cannula 708 is positioned near the trabecular mesh 36 of eye 20.

Figure 8:
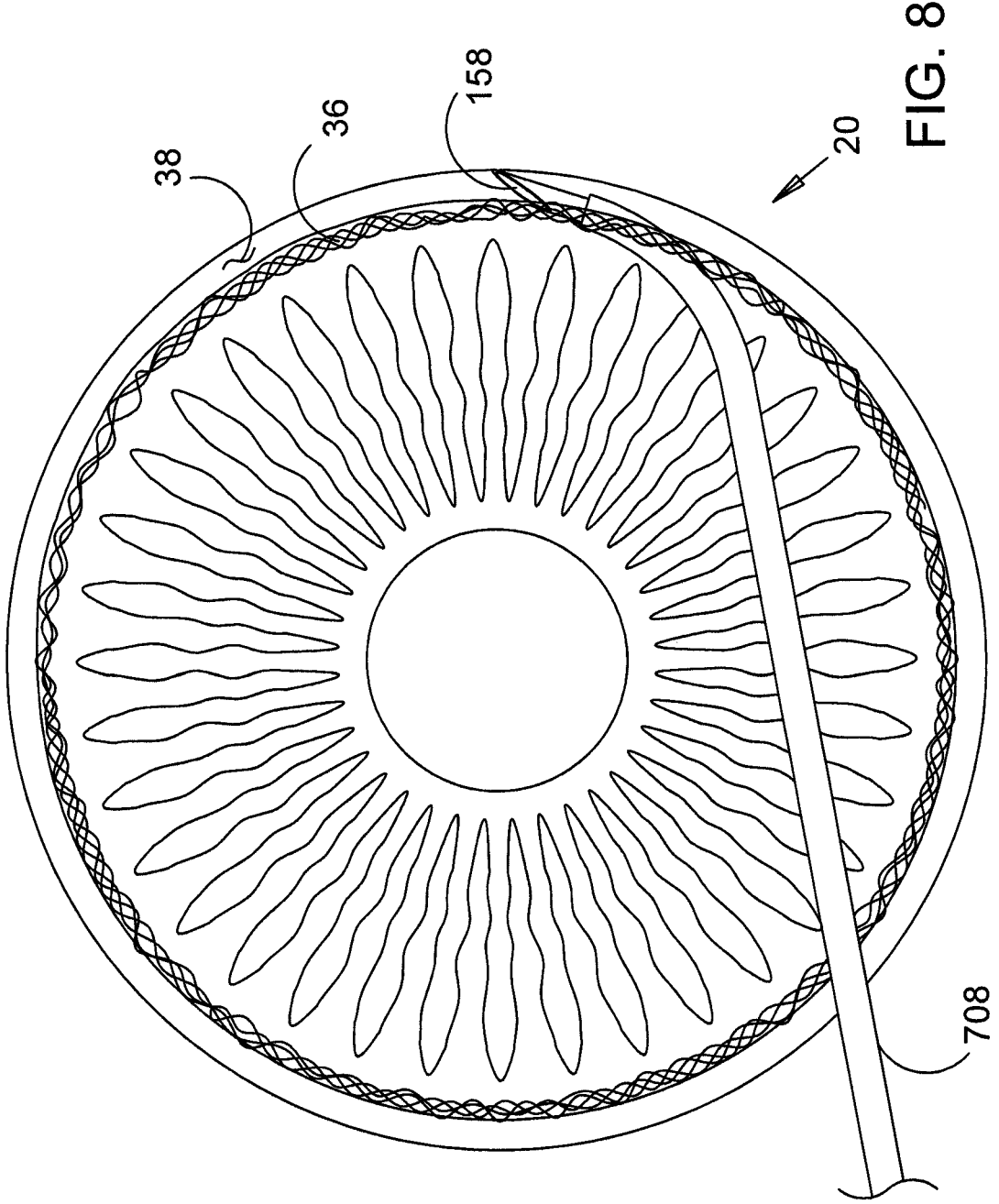
FIG. 8 is a further enlarged plan view illustrating insertion of the ocular implant delivery system cannula into the eye shown in the previous figure.

FIG. 8 is a further enlarged plan view illustrating a portion of eye 20 shown in the previous figure. In the embodiment of FIG. 8, the distal tip of cannula 708 has pierced through trabecular mesh 36. The distal tip of cannula 708 has also pierced the wall of Schlemm's canal 38 so that a distal opening 758 of cannula 708 is disposed in fluid communication with Schlemm's canal 38. In this embodiment, cannula 708 is a rigid curved tube that has a sharp portion at its distal end near the exit port 758. In some embodiments, cannula 708 is curved to achieve substantially tangential entry into Schlemm's canal 38.

Figure 9:
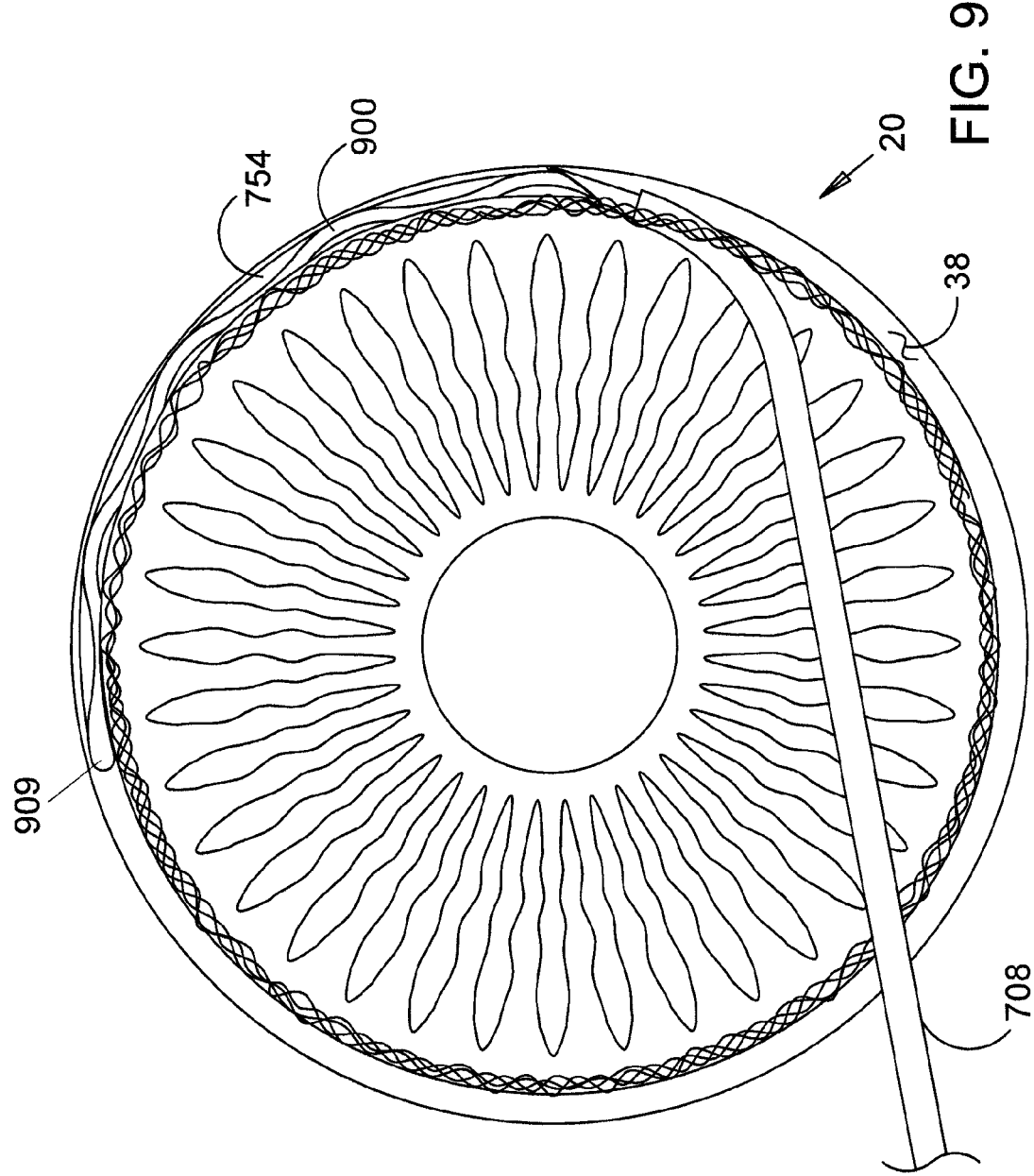
FIG. 9 is an additional plan view of the eye shown in the previous figure showing advancement of an ocular implant through the cannula into Schlemm's canal of the eye.

FIG. 9 is an additional plan view of eye 20 shown in the previous figure. In the embodiment of FIG. 9, an ocular implant 900 has been advanced through distal opening 758 of cannula 708 and into Schlemm's canal 38 of eye 20. With reference to FIG. 9, it will be appreciated that ocular implant 900 is disposed about a core 754 which is movable with ocular implant 900 within cannula 708 as part of an implant advancement mechanism. Core 754 and cannula 708 are part of a delivery system that may be used to deliver ocular implant 900 into Schlemm's canal of eye 20.

Among other functions, one particular function of core 754 is to block the openings formed in ocular implant 900 so as to minimize interference between the implant and tissue within Schlemm's canal 38 as the implant is advanced. The delivery system's advancement mechanism may also include a push tube (not shown) for selectively applying distally directed forces to the proximal end of ocular implant 900. Core 754 may extend proximally into the push tube. A handheld actuator (not shown) may be used to advance the push tube, the core 754 and the ocular implant 900. The handheld actuator may also be used to provide relative motion between the push tube and the core 754. In the embodiment of FIG. 9, ocular implant 900 has a blunt distal end 902 for avoiding damage to ocular tissue. In other embodiments, the blunt distal end may be provided at least in part by core 754. Further details of aspects of ocular implant delivery systems suitable for use with implants and cannulas of this invention may be found in U.S. application Ser. No. 11/943,289, filed Nov. 20, 2007, now U.S. Pat. No. 8,512,404; U.S. application Ser. No. 12/398,847, filed Mar. 5, 2009, now U.S. Pat. No. 8,267,882; U.S. Provisional Application No. 61/224,156, filed Jul. 9, 2009; and U.S. Provisional Application No. 61/224,158, filed Jul. 9, 2009; the disclosures of which are incorporated herein by reference.

Figure 10:
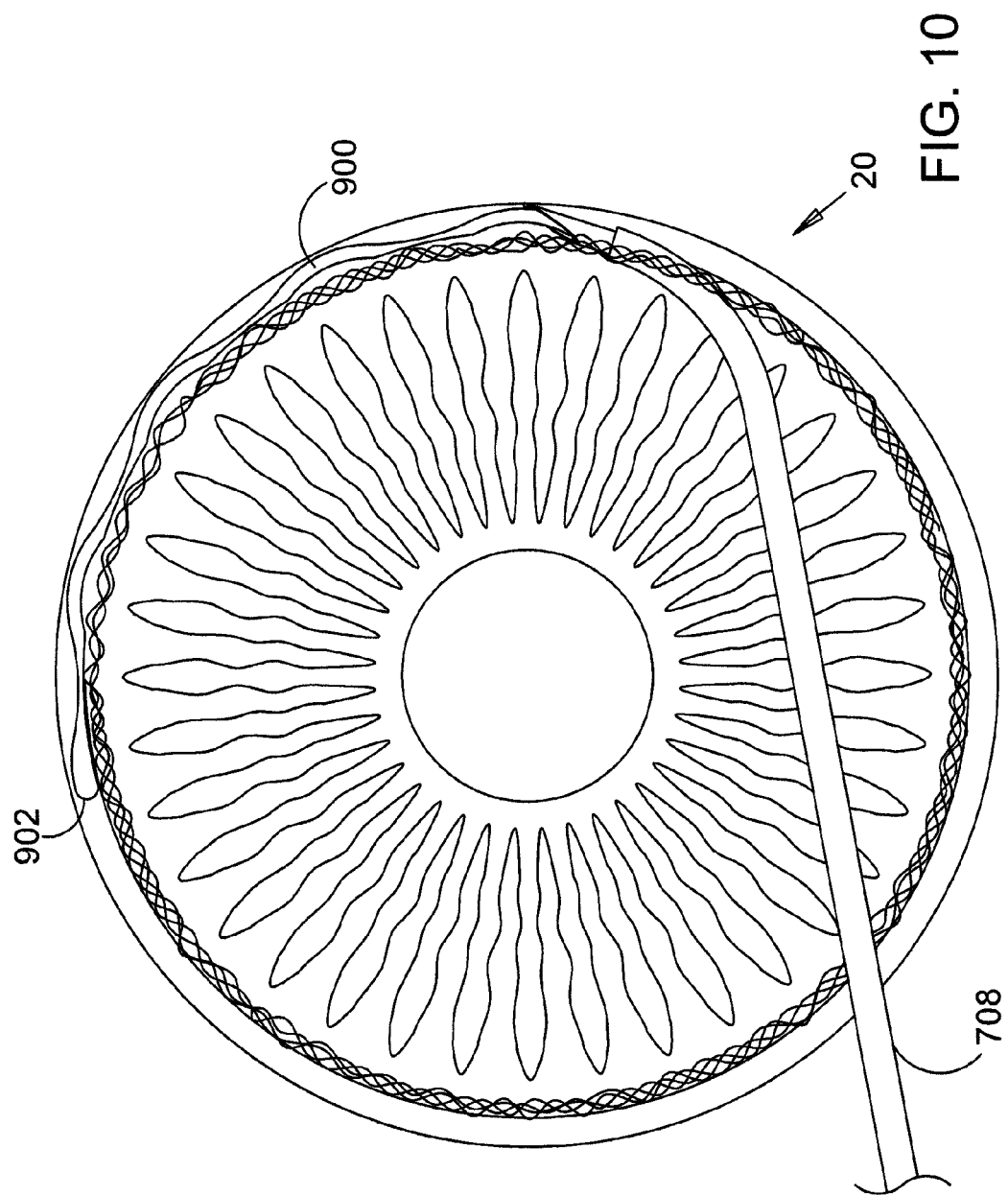
FIG. 10 is an additional plan view of the eye shown in the previous figure. In the embodiment of FIG. 10, a core that was used to position the ocular implant has been withdrawn.

FIG. 10 is an additional plan view of eye 20 shown in the previous figure. In the embodiment of FIG. 10, core 754 has been withdrawn from ocular implant 900. A hand held actuator (not shown) may be used to apply a proximal force to the core to withdraw the core proximally from the ocular implant 900 while a push tube (not shown) applies a distally directed force to hold ocular implant 900 in place. The core, the push tube, and the cannula 708 may then be withdrawn from the eye, leaving the implant in Schlemm's canal with its proximal inlet end within the anterior chamber of eye 20.

Figure 11:
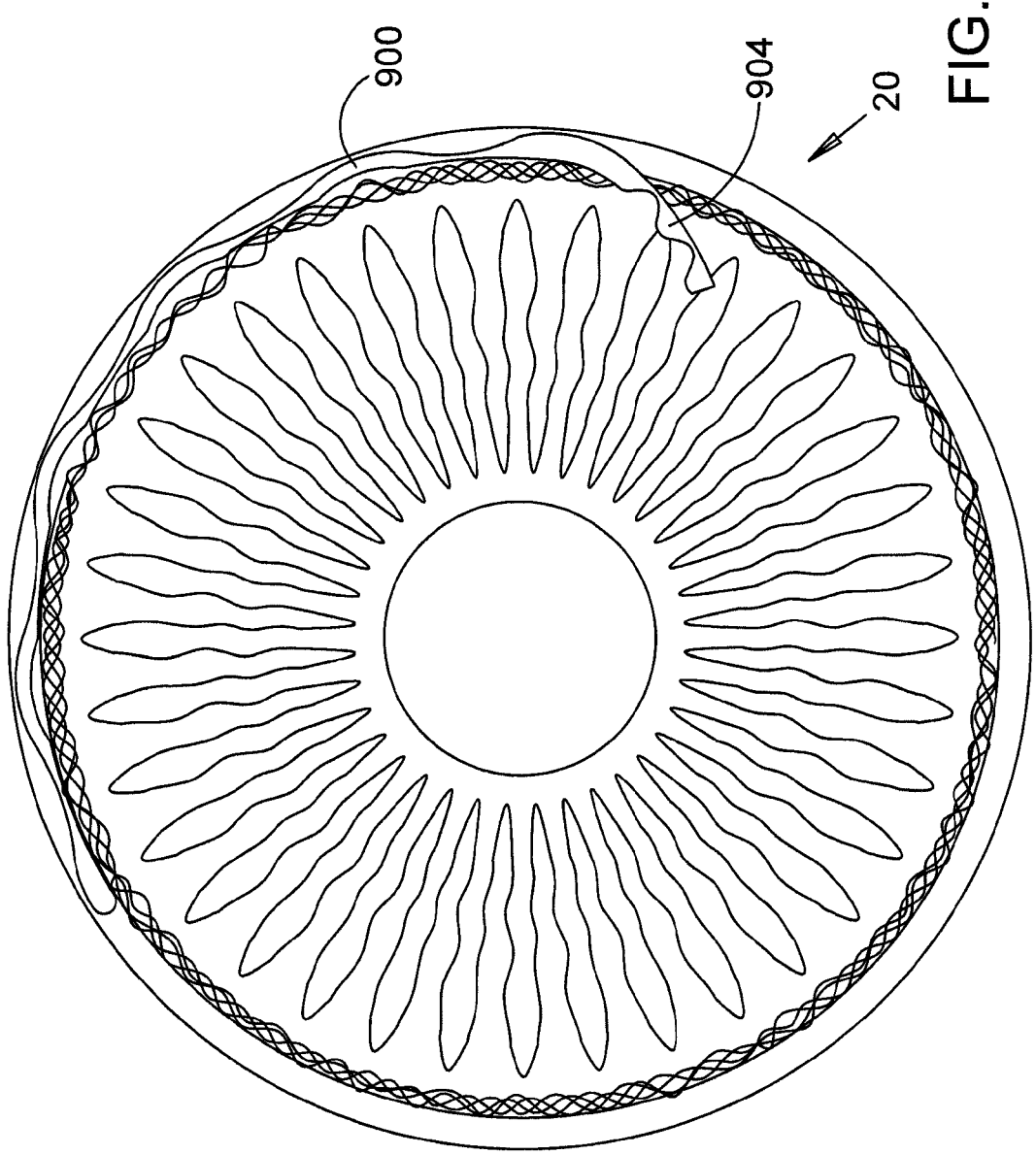
FIG. 11 is a plan view of the eye shown in the previous figure showing the ocular implant in Schlemm's canal after the cannula has been withdrawn.

FIG. 11 is a plan view of eye 20 after cannula 708 has been withdrawn leaving an inlet portion 904 of ocular implant 900 in the anterior chamber and the remainder of implant 900 in Schlemm's canal. The presence of ocular implant 900 in Schlemm's canal may facilitate the flow of aqueous humor out of the anterior chamber. This flow may include axial flow along Schlemm's canal, flow from the anterior chamber into Schlemm's canal, and flow leaving Schlemm's canal via outlets communicating with Schlemm's canal. When in place within the eye, ocular implant 900 will support trabecular mesh tissue and Schlemm's canal tissue and will provide for improved communication between the anterior chamber and Schlemm's canal (via the trabecular meshwork) and between pockets or compartments along Schlemm's canal.

Figure 12:
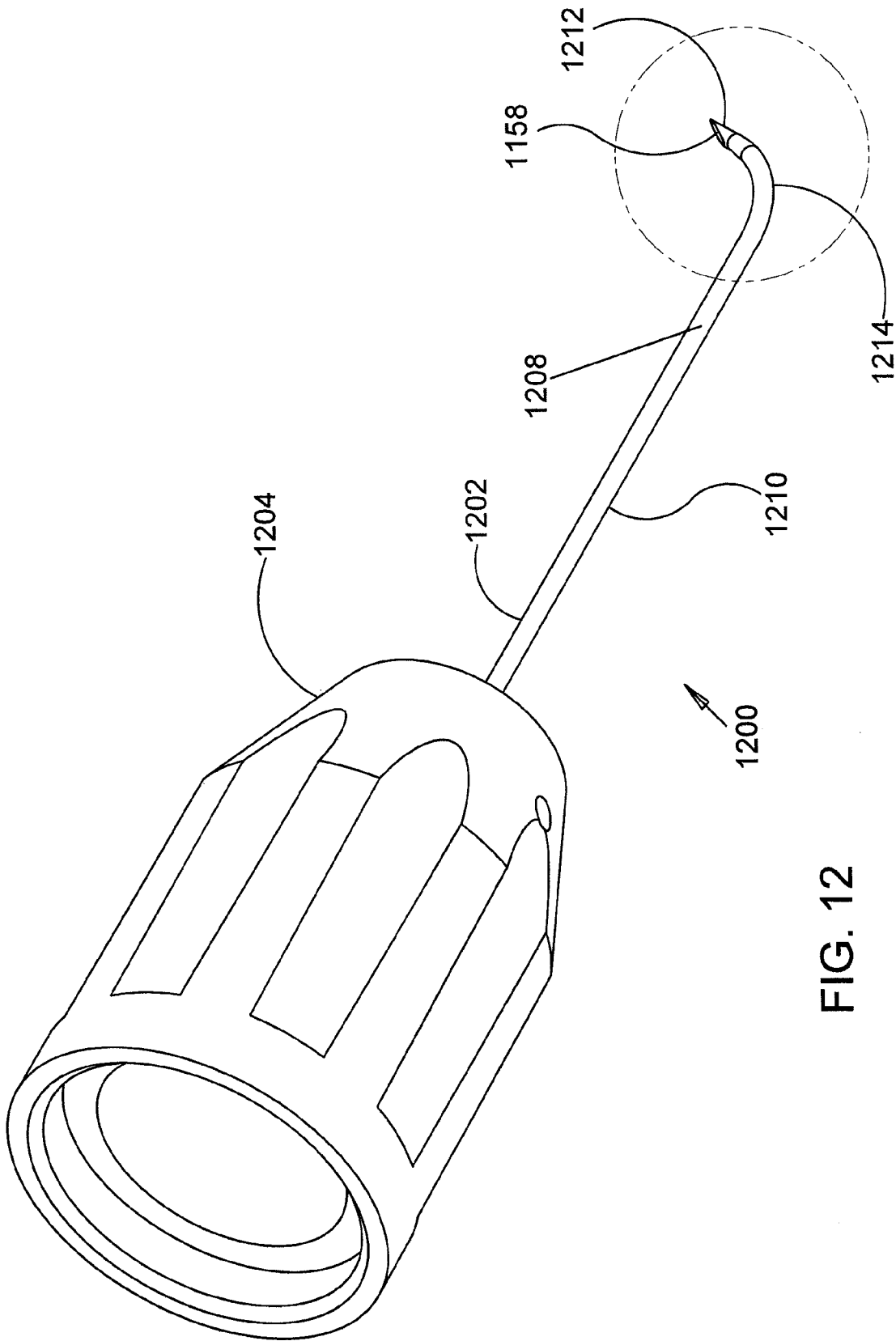
FIG. 12 is a perspective view of an exemplary cannula assembly.

FIG. 12 is a perspective view of an exemplary cannula assembly 1200. Cannula assembly 1200 comprises a tubular member 1202 that is fixed to a hub 1204. Tubular member 1202 defines a proximal opening 1206, a distal opening 1158, and a lumen 1208 that extends between proximal opening 1206 and distal opening 1158. Tubular member 1202 also comprises a proximal portion 1210, a distal portion 1212, and a bent portion 1214 disposed between proximal portion 1210 and distal portion 1212.

Figure 13:
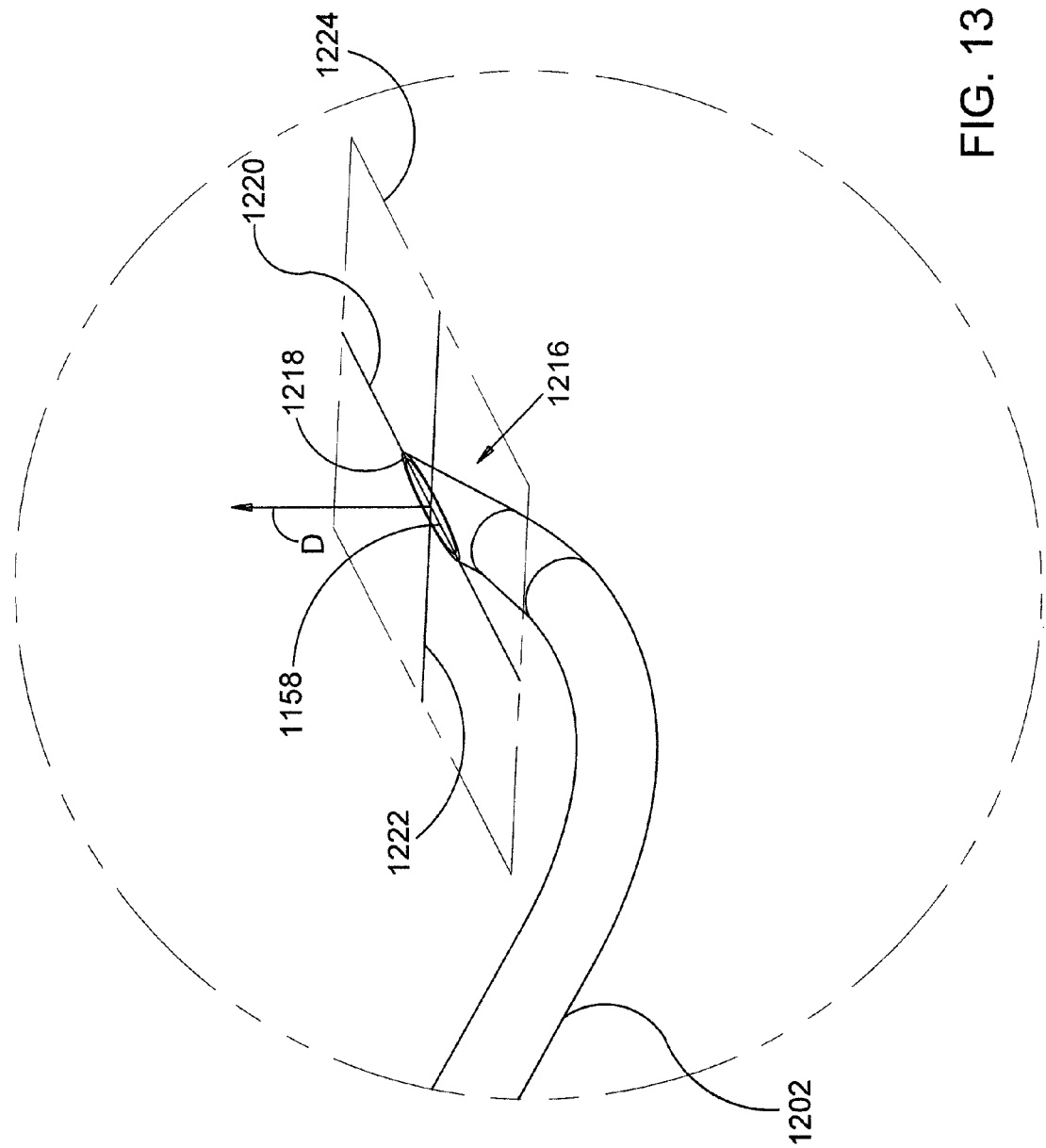
FIG. 13 is an enlarged perspective view showing a portion of a tubular member of the cannula shown in the previous figure.

FIG. 13 is an enlarged perspective view showing a portion of tubular member 1202 shown in the previous figure. With reference to FIG. 13, it will be appreciated that tubular member 1202 comprises a beveled distal tip 1216 having a distal opening surface 1218. In the exemplary embodiment of FIG. 13, beveled distal tip 1216 defines a distal opening 1158 having a generally elliptical shape. A major axis 1220 and a minor axis 1222 of distal opening 1158 are illustrated using dashed lines in FIG. 13. For purposes of illustration, major axis 1220 and minor axis 1222 each extend beyond distal opening 1158 in FIG. 13.

In the exemplary embodiment of FIG. 13, major axis 1220 and minor axis 1222 define an exit plane 1224. Distal opening 1158 opens in a direction D that is orthogonal to exit plane 1224. Direction D is illustrated using an arrow in FIG. 13. In some useful embodiments, an imaginary line representing direction D intersects the cornea of the eye when the when the tubular member is extending through the cornea and the distal opening is fluidly communicating with Schlemm's canal of the eye.

Figure 14:
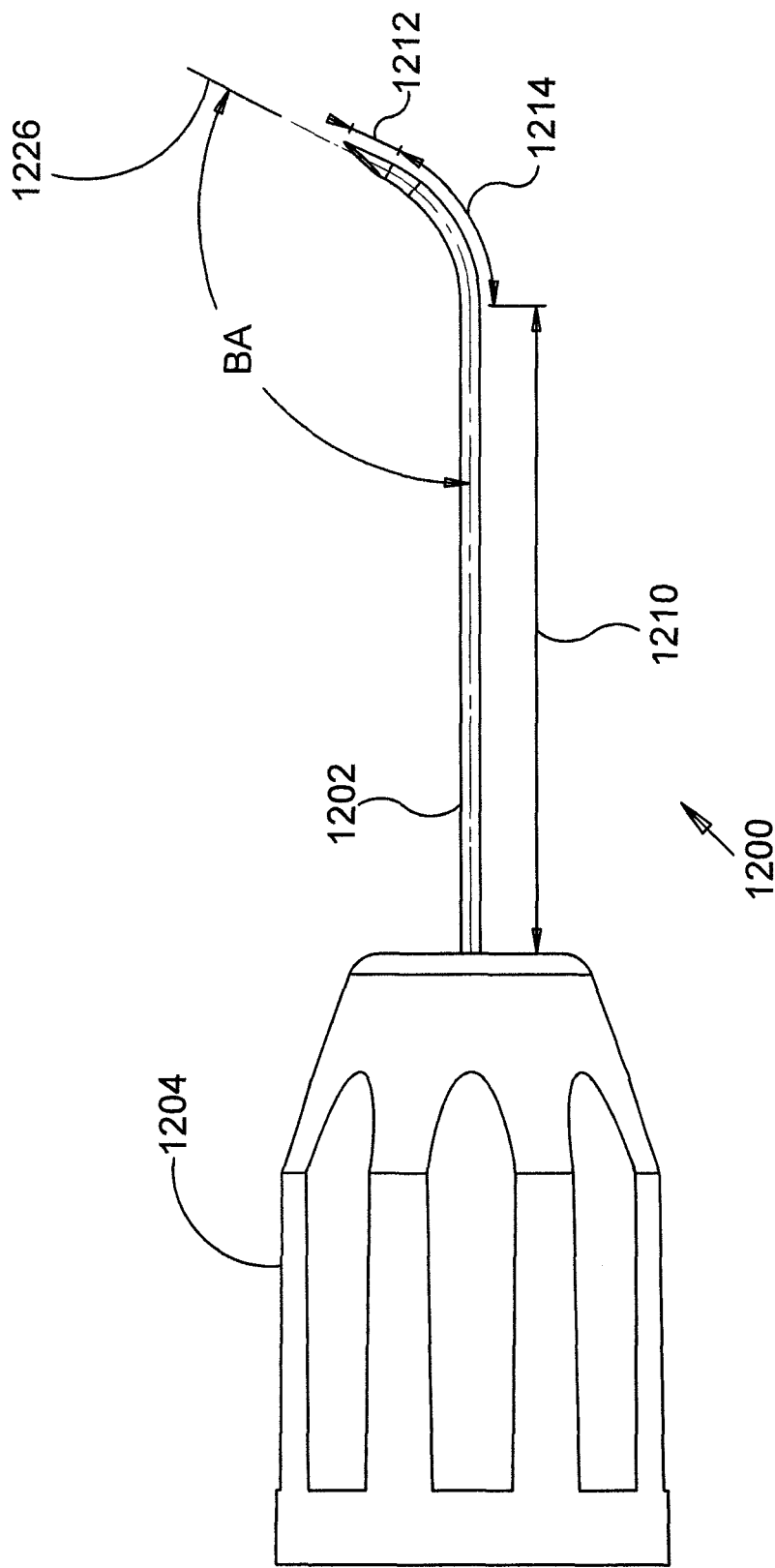
FIG. 14 is a plan view further illustrating the cannula assembly of FIG. 12.

FIG. 14 is a plan view further illustrating cannula assembly 1200. With reference to FIG. 14, it will be appreciated that tubular member 1202 of cannula assembly 1200 comprises a proximal portion 1210, a distal portion 1212, and a bent portion 1214 disposed between proximal portion 1220 and distal portion 1222. In the exemplary embodiment of FIG. 14, a hub 1204 is fixed to proximal portion 1210 of tubular member 1202. With reference to FIG. 14, it will be appreciated that tubular member 1202 has a central axis 1226. Central axis 1226 of FIG. 14 has a curved portion and straight portions. In FIG. 14, a bend angle BA is shown extending between a first straight portion of central axis 1226 and a second straight portion of central axis 1226.

In some useful embodiments, bent portion 1214 of tubular member 1202 is dimensioned to achieve substantially tangential entry into Schlemm's canal of a human eye. In these useful embodiments, bent portion 1214 may have a radius of curvature between about 0.05 inches and about 0.3 inches, and an angular span between about 105 degrees and about 165 degrees. In one exemplary embodiment, bent portion 1214 has a bend radius of about 0.125 inches (measured to the tube centerline) and an angular span of about 132.5 degrees. In this exemplary embodiment, distal portion 1212 may have a length of about 0.044 inches and proximal portion 1210 may have a length of about 0.727 inches.

Figure 15:
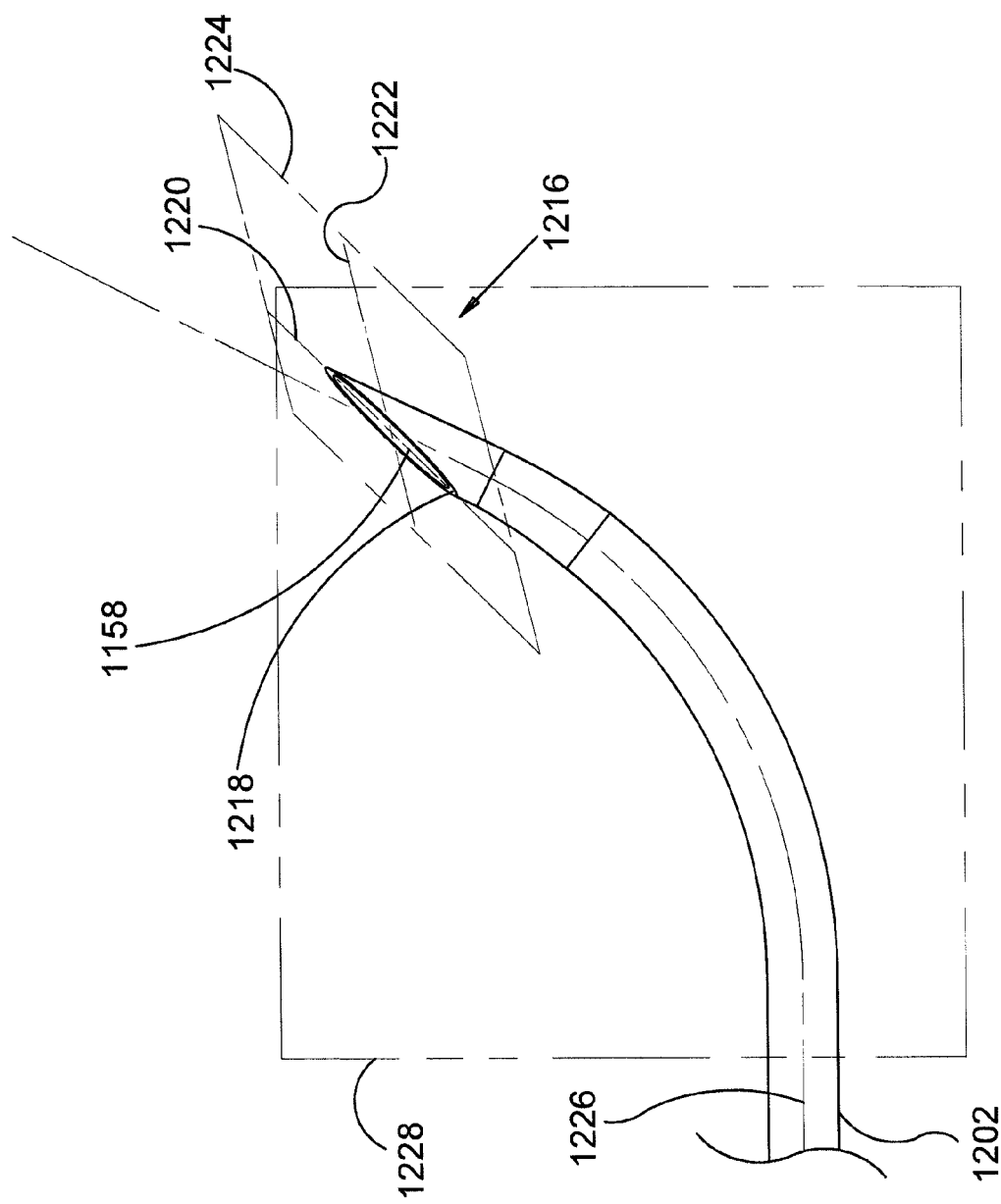
FIG. 15 is an enlarged plan view showing a portion of the tubular member shown in the previous figure.

FIG. 15 is an enlarged plan view showing a portion of tubular member 1202 shown in the previous figure. With reference to FIG. 15, it will be appreciated that tubular member 1202 has a central axis 1226 defining a bend plane 1228. Central axis 1226 of FIG. 15 has a curved portion and straight portions. Tubular member 1202 of FIG. 15 also comprises a beveled distal tip 1216 having a distal opening surface 1228. In the exemplary embodiment of FIG. 15, beveled distal tip 1216 defines a distal opening 1158 having a generally elliptical shape. A major axis 1220 and a minor axis 1222 of distal opening 1158 are illustrated using dashed lines in FIG. 15.

For purposes of illustration, major axis 1220 and minor axis 1222 each extend beyond distal opening 1158 in FIG. 15. In the exemplary embodiment of FIG. 15, major axis 1220 and minor axis 1222 define an exit plane 1224. In FIG. 15, exit plane 1224 is shown intersecting bend plane 1228. With reference to FIG. 15, it will be appreciated that exit plane 1224 is generally skewed relative to bend plane 1228. That is, the plane 1222 of distal opening surface 1228 meets plane 1228 of the cannula curve at an angle other than 90 degrees.

Figure 16:
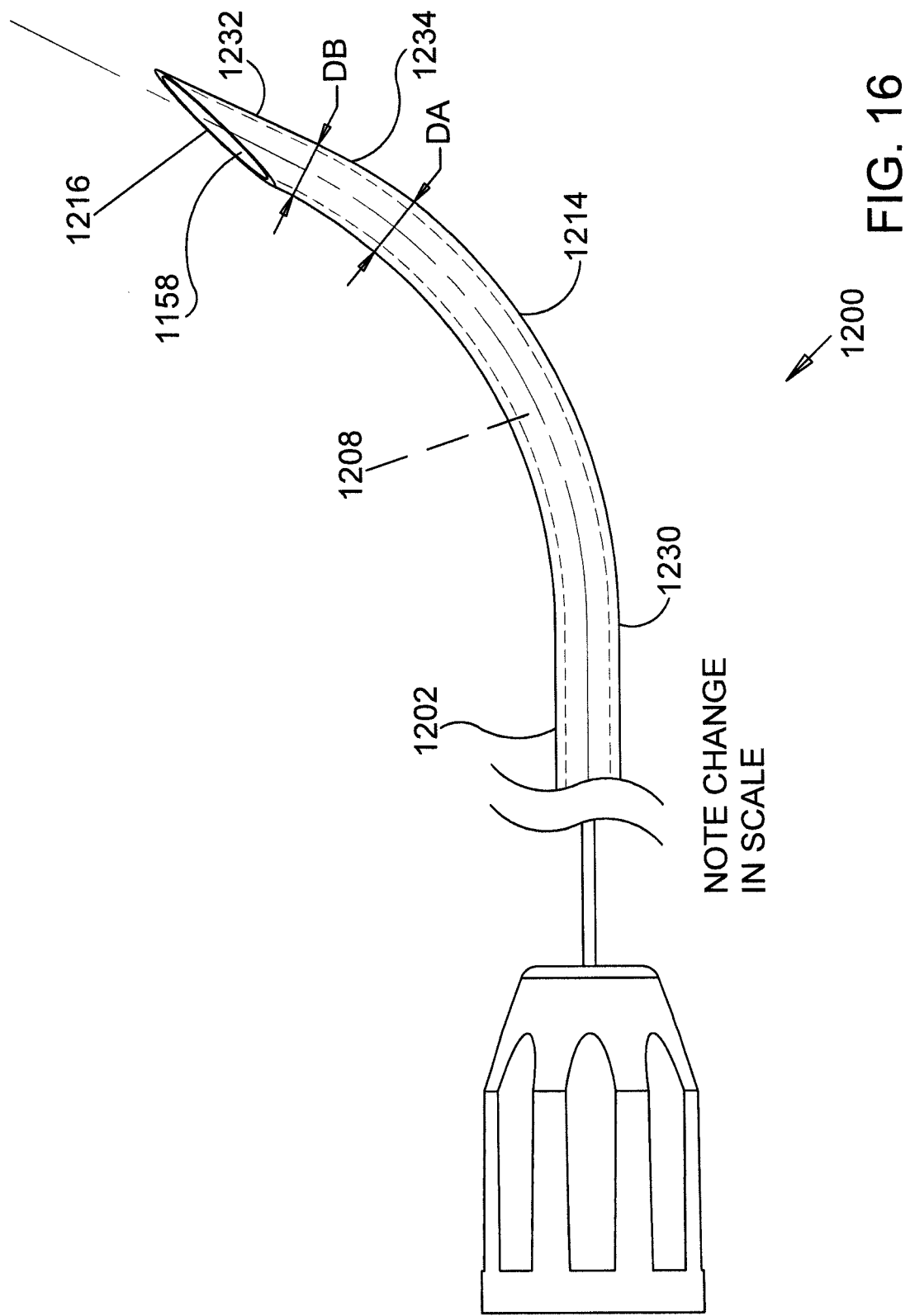
FIG. 16 is a plan view further illustrating the cannula assembly of FIG. 12.

FIG. 16 is a plan view further illustrating cannula assembly 1200. With reference to FIG. 16, it will be appreciated that tubular member 1202 of cannula assembly 1200 comprises a first portion 1230 having a first diameter DA, a second portion 1232 having a second diameter DB, and a tapered portion 1234 disposed between first portion 1230 and second portion 1232.

In the exemplary embodiment of FIG. 16, first diameter DA is greater than second diameter DB, and tapered portion 1234 transitions between first diameter DA and second diameter DB. In some useful embodiments, tapered portion 1234 has an average taper ratio between about 0.01 and about 0.12. In one exemplary embodiment, tapered portion 1234 has an average taper ratio of about 0.068.

Tubular member 1202 defines a proximal opening (not shown), a distal opening 1158, and a lumen 1208 that extends between the proximal opening and the distal opening. In the exemplary embodiment of FIG. 16, lumen 1208 has a generally circular cross-sectional shape. In some useful embodiments, lumen 1208 has a diameter that is substantially uniform along the length of tubular member 1202. This configuration reduces the likelihood that an ocular implant advanced through lumen 1208 will become hung up during delivery through the lumen.

In some useful embodiments, second diameter DB is dimensioned so that distal opening 1158 can be placed in fluid communication with Schlemm's canal of a human eye. Also in some useful embodiments, first diameter DA is dimensioned to provide a desirable level of structural support when tubular member 1202 is advanced through the cornea of a human eye and the distal end of beveled tip 1216 is inserted into Schlemm's canal.

In some useful embodiments first diameter DA is between about 0.010 and about 0.030 inches and second diameter DB is between about 0.005 and about 0.020. In one exemplary embodiment, first diameter DA is about 0.018 inches, second diameter DB is about 0.016, and the diameter of lumen 1208 is about 0.0135 inches. With reference to FIG. 16, it will be appreciated that tubular member 1202 comprises a bent portion 1214. In the exemplary embodiment of FIG. 16, tapered portion 1234 is extends along a portion of bent portion 1214 of tubular member 1202.

FIG. 17A and FIG. 17B are plan views further illustrating tubular member 1202 of cannula assembly 1200. With reference to FIG. 17A, it will be appreciated that tubular member 1202 comprises a beveled distal tip 1216 having a distal opening surface 1218. In the exemplary embodiment of FIG. 17A, beveled distal tip 1216 defines a distal opening 1158 having a generally elliptical shape. A major axis 1220 and a minor axis 1222 of distal opening 1158 are illustrated using dashed lines in FIG. 17A. For purposes of illustration, major axis 1220 and minor axis 1222 each extend beyond distal opening 158 in FIG. 17A.

FIG. 17B is an additional plan view showing the portion of tubular member 1202 shown in FIG. 17A. FIG. 17B is taken from a viewpoint that is generally orthogonal to the viewpoint used to create FIG. 17A. With reference to FIG. 17B, it will be appreciated that tubular member 1202 has a central axis 1226 that includes both straight portions and curved portions.

Major axis 1220 of distal opening 1158 and central axis 1226 of tubular member 1202 define a pitch angle PA of beveled distal tip 1216. In some useful embodiments, pitch angle PA is steep enough to tent open tissue (e.g., trabecular mesh and the wall of Schlemm's canal) when the distal end of beveled tip 1216 is inserted into Schlemm's canal. Also in some useful embodiments, pitch angle PA is shallow enough to prevent tearing or cutting of tissue when the distal end of beveled tip 1216 is inserted into Schlemm's canal. In some useful embodiments, pitch angle PA is between about 5 degrees and about 35 degrees. In some particularly useful embodiments, pitch angle PA is greater than about 15 degrees and less than about 25 degrees. In one exemplary embodiment, pitch angle PA is about 20 degrees.

Figures 18A, 18B:
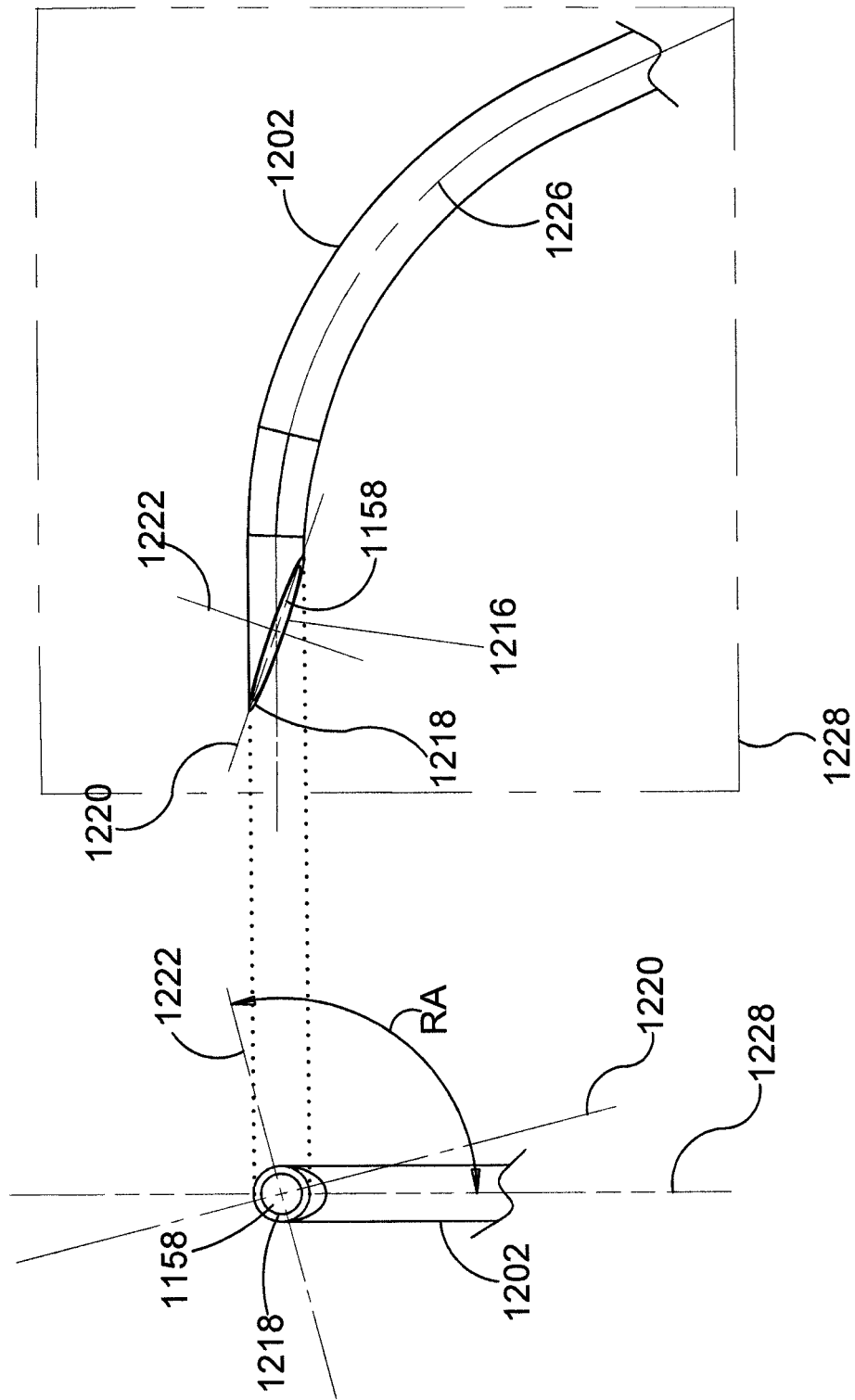
FIGS. 18A and 18B are plan views further illustrating the tubular member of the cannula assembly shown in FIG. 12.

FIG. 18A and FIG. 18B are plan views further illustrating tubular member 1202 of cannula assembly 1200. With reference to FIG. 18B, it will be appreciated that tubular member 1202 has a central axis 1226 defining a bend plane 1228. Central axis 1226 of FIG. 18B has a curved portion and straight portions. In the embodiment of FIG. 18B, tubular member 1202 also comprises a beveled distal tip 1216 having a distal opening surface 1218. In the exemplary embodiment of FIG. 18B, beveled distal tip 1216 defines a distal opening 1158 having a generally elliptical shape. A major axis 1220 and a minor axis 1222 of distal opening 1158 are illustrated using dashed lines in FIG. 18B.

FIG. 18A is an axial plan view showing tubular member 1202 and distal opening surface 1218. FIG. 18A is taken from a viewpoint that is generally orthogonal to the viewpoint used to create FIG. 18B. Bend plane 1228, major axis 1220 and minor axis 1222 are illustrated using dashed lines in FIG. 18A. With reference to FIG. 18A, it will be appreciated that minor axis 1222 of distal opening 1158 and bend plane 1228 define a roll angle RA.

In some useful embodiments, roll angle RA is selected so that a physician using the cannula assembly can see distal opening 1158 when the tubular member 1202 is extending through the cornea of a human eye and the distal end of beveled distal tip 1216 is inserted into Schlemm's canal. In other words, the plane of distal opening surface 1218 meets bend plane 1228 at an angle other than 90 degrees. Also in some useful embodiments, roll angle RA is selected so that distal end of beveled distal tip 1216 is the first part of tubular member 1202 to touch tissue when the tubular member 1202 is extending through the cornea of a human eye and the distal end of beveled distal tip 1216 is inserted into Schlemm's canal.

Additionally, roll angle RA may be selected so that an ocular implant travels over the point of beveled distal tip 1216 as the ocular implant is advanced out of distal opening 1158 and into Schlemm's canal. In some useful embodiments, roll angle RA is greater than about 100 degrees and less than about 110 degrees. In one exemplary embodiment, roll angle RA is about 105 degrees.

Figure 19:
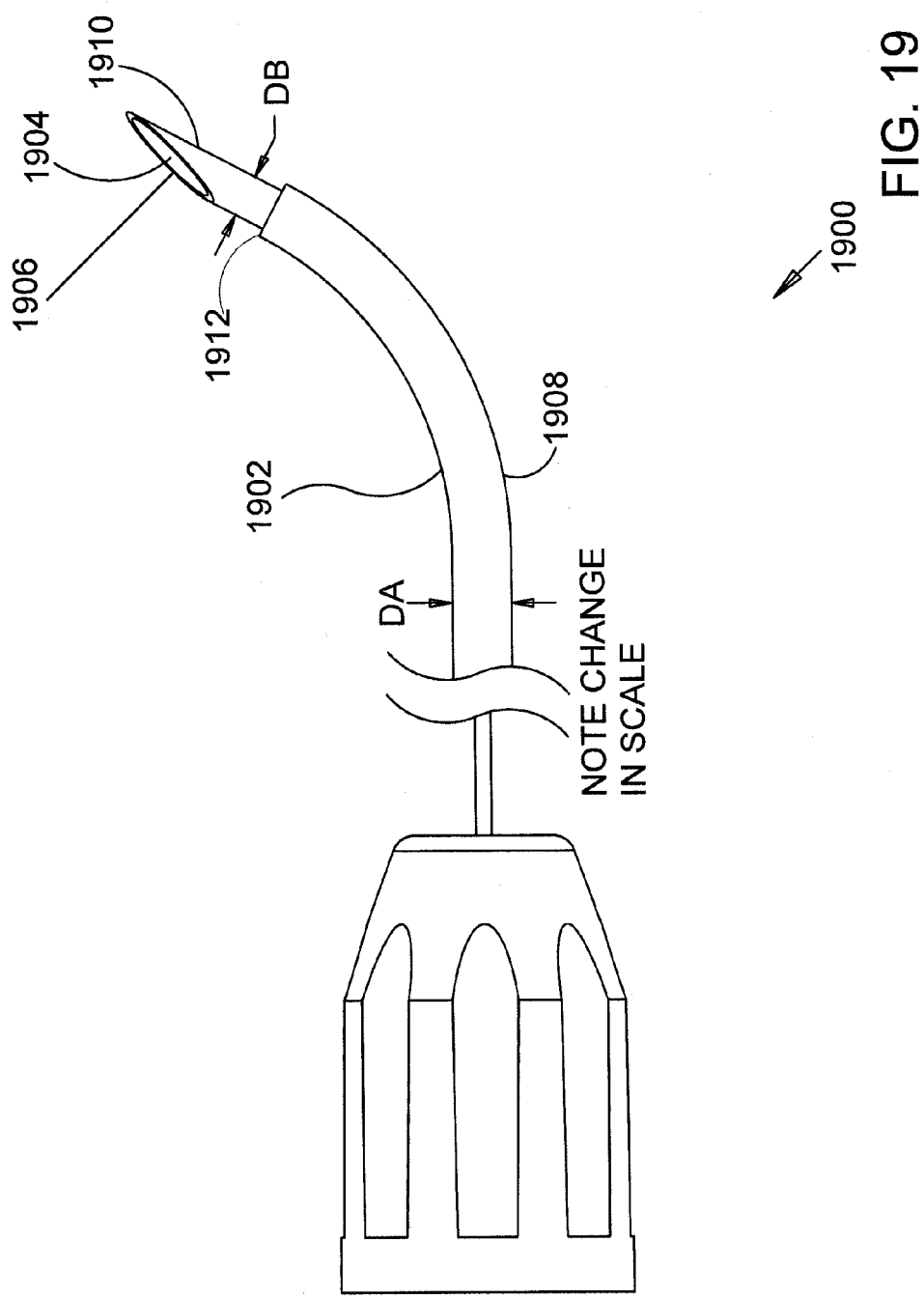
FIG. 19 is a plan view illustrating an alternate embodiment of a cannula assembly.

FIG. 19 is a plan view illustrating an alternate exemplary embodiment of an ocular implant delivery system cannula assembly. With reference to FIG. 19, it will be appreciated that tubular member 1902 of cannula assembly 1900 comprises a first portion 1908 having a first diameter DA and a second portion 1910 having a second diameter DB. A step 1912 is disposed between first portion 1908 and second portion 1910. In some useful embodiments, second diameter DB is dimensioned so that distal opening 1904 can be placed in fluid communication with Schlemm's canal of a human eye. Also in some useful embodiments, first diameter DA is dimensioned to provide a desirable level of structural support when tubular member 1902 is advance through the cornea of a human eye and the distal end of beveled distal tip 1906 is inserted into Schlemm's canal. In some useful embodiments first diameter DA is between about 0.010 and about 0.030 inches and second diameter DB is between about 0.005 and about 0.020. In one exemplary embodiment, first diameter DA is about 0.018 inches, second diameter DB is about 0.016, and the diameter of the inner lumen of tubular member 1902 is about 0.0135 inches.

Figure 20:
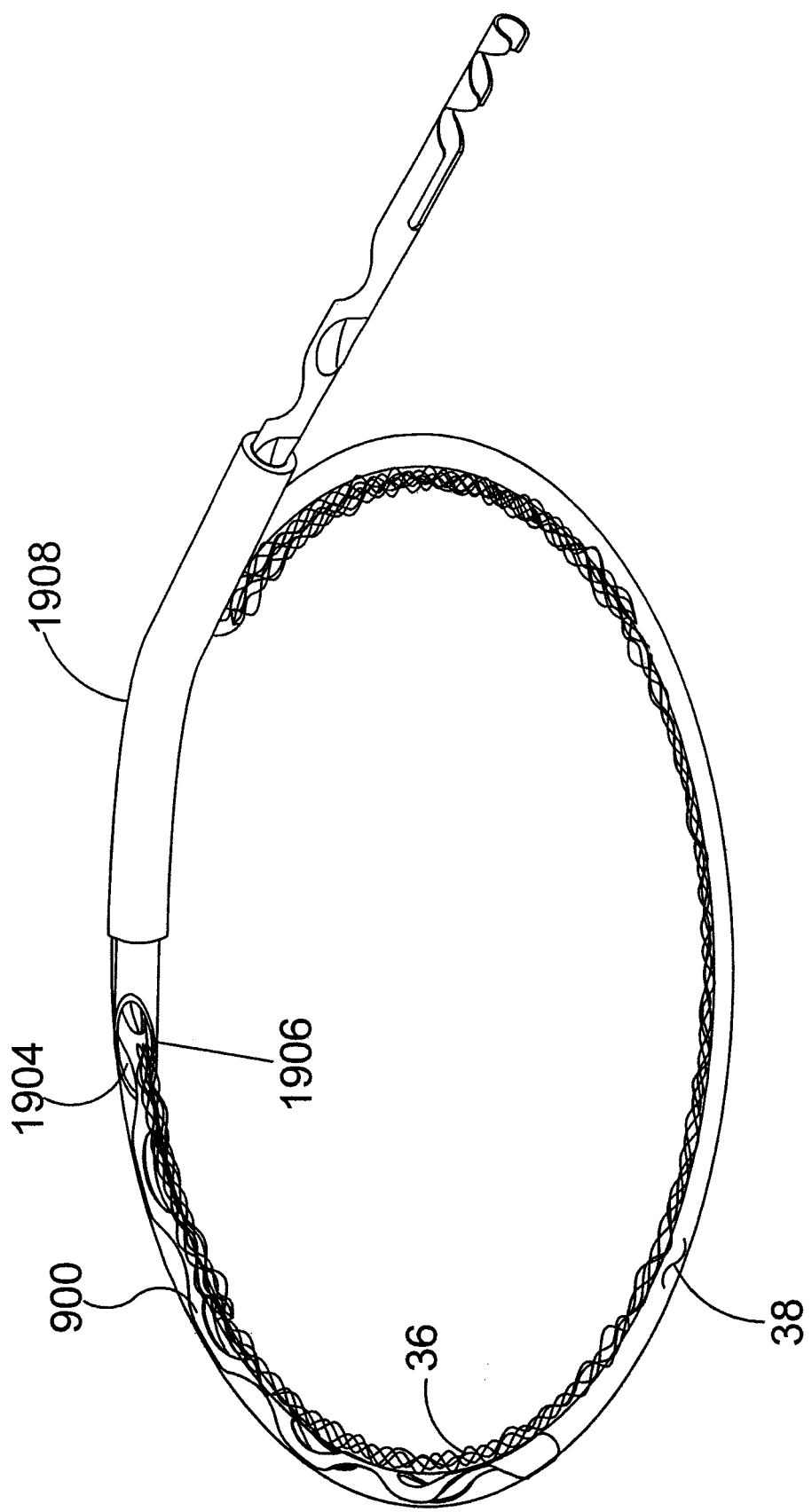
FIG. 20 is a stylized perspective view showing a portion of the tubular member shown in the previous figure delivering an ocular implant into Schlemm's canal.

FIG. 20 is a stylized perspective view showing a portion of tubular member 1908 shown in the previous figure. In FIG. 20, an ocular implant 900 is shown extending through distal opening 1904 of tubular member 1908 and into Schlemm's canal 38 of an eye. The distal end of beveled distal tip 1906 has penetrated the trabecular mesh 36 of the eye, and distal opening 1904 is in fluid communication with Schlemm's canal 38. In the embodiment of FIG. 20, ocular implant 900 is oriented so that the longitudinal channel of ocular implant 900 opens radially outward.

Figure 21:
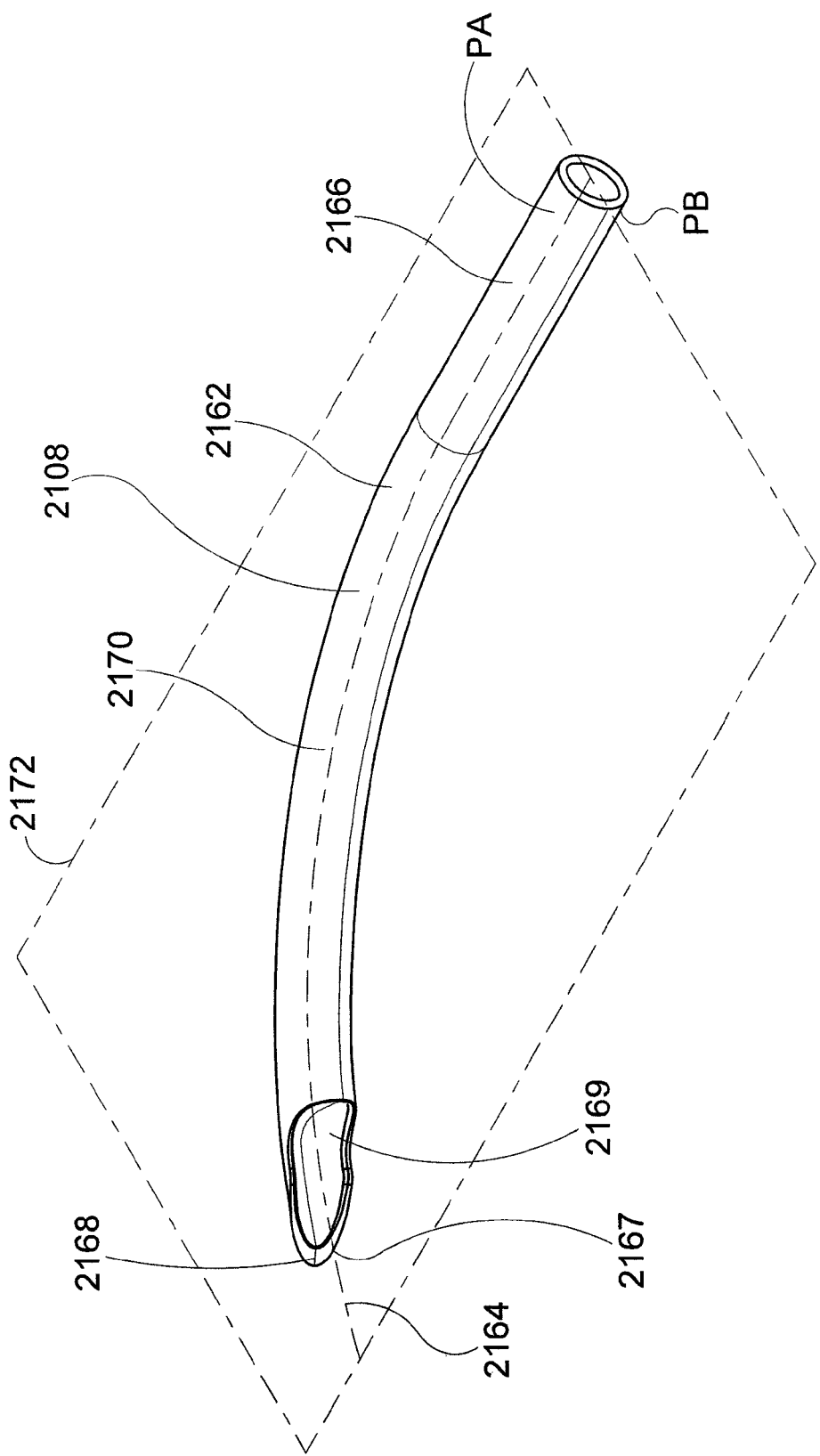
FIG. 21 is a perspective view of another embodiment of an ocular implant delivery system cannula in accordance with this invention.

FIG. 21 is a perspective view of a cannula 2108 in accordance with the present detailed description. Cannula 2108 of FIG. 21 comprises a generally tubular member 2162 having a central axis 2164. Generally tubular member 2162 of FIG. 21 comprises a proximal portion 2166, a distal end 2168, and a distal portion 2170 extending between distal end 2168 and proximal portion 2166. A distal opening surface 2167 surrounds a distal opening 2169.

In the exemplary embodiment of FIG. 21, proximal portion 2166 of cannula 2108 is substantially straight, distal portion 2170 of cannula 2108 is curved, and central axis 2164 defines a curvature plane 2172. Curvature plane 2172 may be referred to as a plane of curvature. With reference to FIG. 21, it will be appreciated that curvature plane 2172 divides cannula 2108 into a first portion PA and a second portion PB. In the exemplary embodiment of FIG. 21, second portion PB is substantially a mirror image of first portion PA. In FIG. 21, distal portion 2170 is shown extending between distal end 2168 and proximal portion 2166 with no intervening elements. In the exemplary embodiment of FIG. 21, distal portion 2170 is curved along its entire length.

An exemplary method in accordance with this detailed description may include the step of advancing the distal end 2168 of cannula 2108 through the cornea of a human eye so that distal end 2168 is disposed in the anterior chamber of the eye. Cannula 2108 may then be used to access Schlemm's canal of the eye, for example, by piercing the wall of Schlemm's canal with the distal end 2168 of cannula 108. Distal opening 2169 of cannula 2108 may be placed in fluid communication with a lumen defined by Schlemm's canal. The ocular implant may be advanced out of a distal port of the cannula and into Schlemm's canal.

Figure 22:
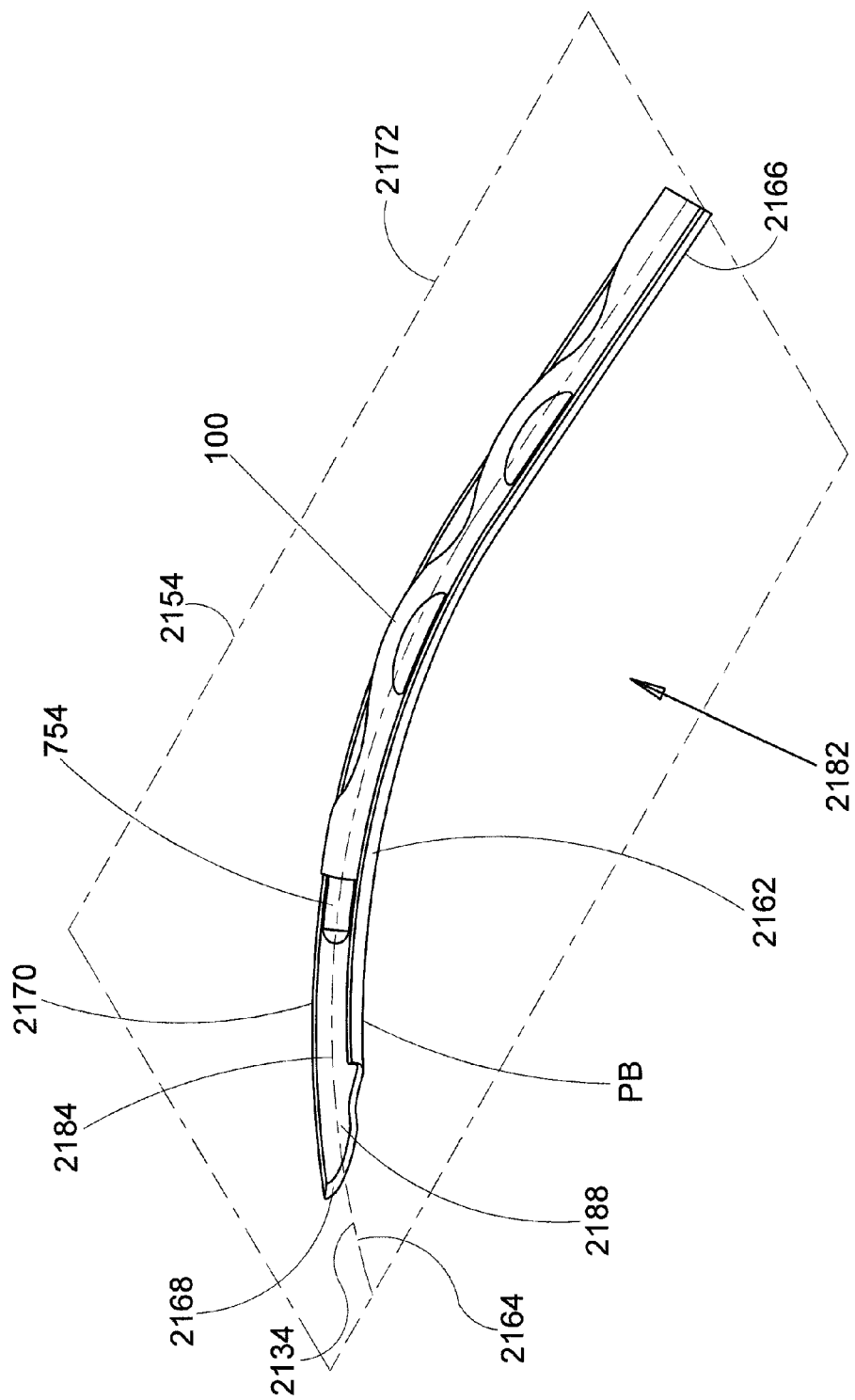
FIG. 22 is a partial sectional and perspective view showing portions of an ocular implant delivery system into which an ocular implant has been loaded.

FIG. 22 is a perspective view of an assembly 2182 including cannula 2108 shown in the previous figure. For purposes of illustration, cannula 2108 is cross-sectionally illustrated in FIG. 22. In FIG. 22, an ocular implant 100 can be seen resting in a lumen 2184 defined by cannula 2108. In the exemplary embodiment of FIG. 22, ocular implant 100 is disposed about a core 754.

Ocular implant 100 extends along a generally curved longitudinal axis 2134. Longitudinal axis 2134 defines a first plane 2154. In the embodiment of FIG. 22, the flexibility of ocular implant 100 is at a maximum when it is bending along first plane 2154, and implant 100 has less flexibility when bending along a plane other than first plane 2154 (e.g., a plane that intersects first plane 2154). Accordingly, first plane 2154 may be generally referred to as a plane of preferential bending.

Cannula 2108 of FIG. 22 comprises a generally tubular member 2162 having a central axis 2164. Generally tubular member 2162 of FIG. 22 comprises a proximal portion 2166, a distal end 2168, and a distal portion 2170 extending between distal end 2168 and proximal portion 2166. In the exemplary embodiment of FIG. 22, proximal portion 2166 of cannula 2108 is substantially straight.

In the embodiment of FIG. 22, central axis 2164 of cannula 2108 is coaxial with the longitudinal axis 2134 of ocular implant 100. With reference to FIG. 22, it will be appreciated that distal portion 2170 of cannula 2108 is curved so that central axis 2164 of cannula 2108 defines a curvature plane 2172. Curvature plane 2172 may be referred to as a plane of curvature. With reference to FIG. 22, it will be appreciated that curvature plane 2172 divides cannula 2108 into a first portion and a second portion PB. Only second portion PB of cannula 2108 is shown in the illustrative embodiment of FIG. 22. In this embodiment, curvature plane 2172 is coincident with first plane 2154.

Figure 23:
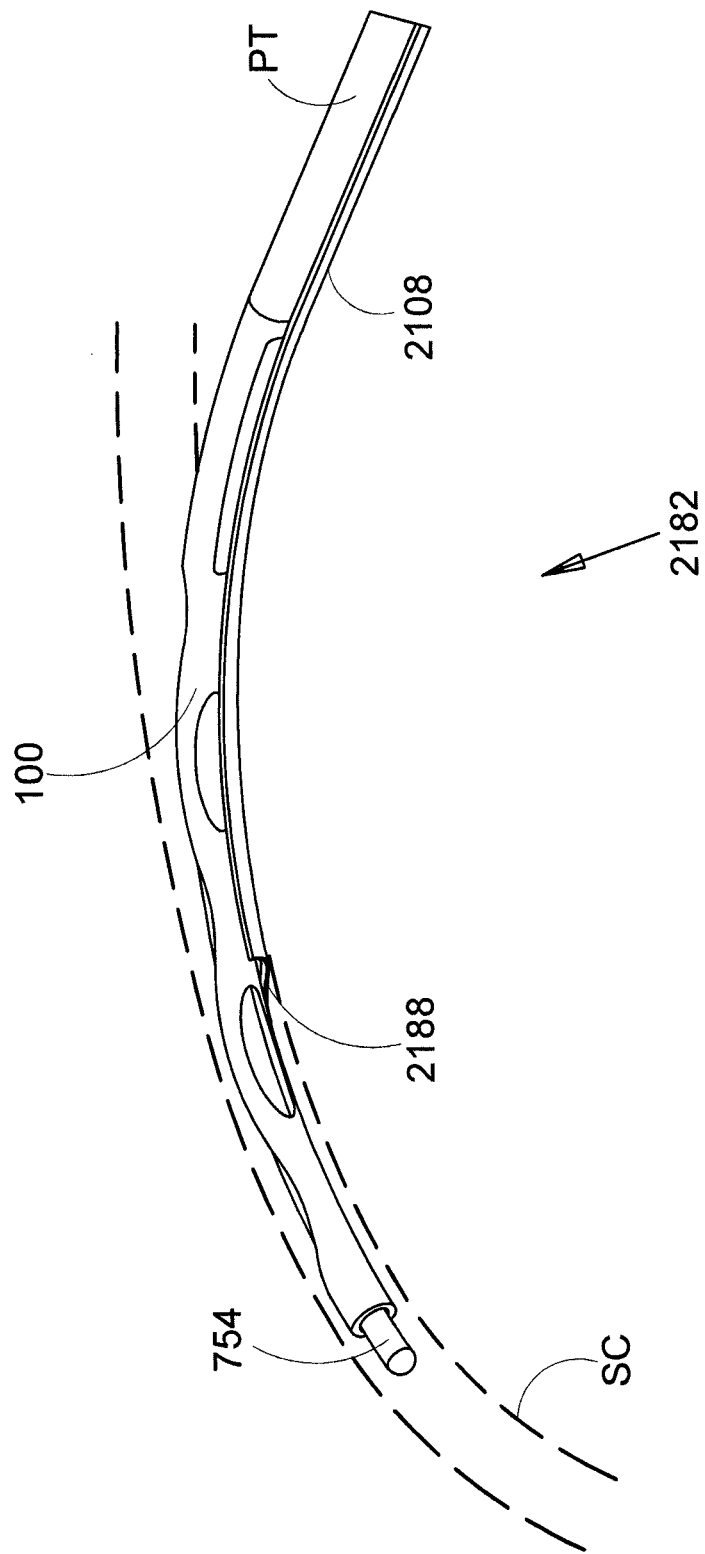
FIG. 23 is an additional perspective view of the assembly shown in FIG. 22 showing delivery of the ocular implant into Schlemm's canal.

FIG. 23 is an additional perspective view of assembly 2182 shown in the previous figure. In FIG. 23, core 754 of the delivery system's advancement mechanism and ocular implant 100 are shown extending through distal port 2188 of cannula 2108. With reference to the previous figure, it will be appreciated that core 754 and ocular implant 100 have been moved in a distal direction relative to the position of those elements shown previously. Schlemm's canal SC of an eye is illustrated using dashed lines in FIG. 23. In the embodiment of FIG. 23, a portion of ocular implant 100 has been advanced into Schlemm's canal SC. Ocular implant 100 is oriented so as to bend most easily in a direction conforming with the natural curvature of Schlemm's canal SC. In FIG. 23, a distal end of a push tube PT of the delivery system's advancement mechanism is shown contacting a proximal end of ocular implant 100. In the embodiment of FIG. 23, push tube PT is disposed in the lumen defined by cannula 2108.

Figure 24:
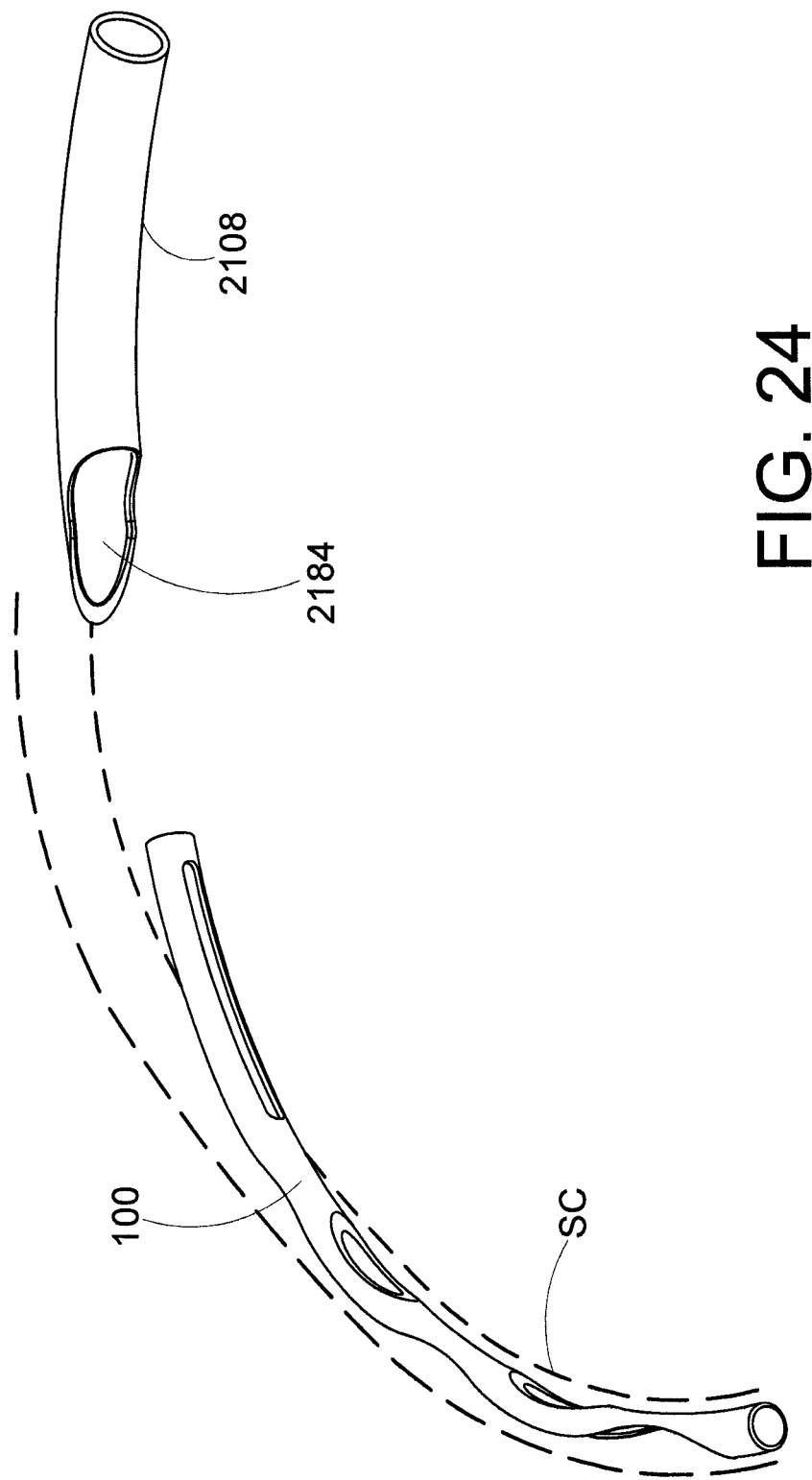
FIG. 24 is an additional perspective view showing portions of the implant and the cannula shown in FIGS. 22 and 23.

FIG. 24 is an additional perspective view showing ocular implant 100 and cannula 2108 shown in the previous figure. With reference to FIG. 24, it will be appreciated that ocular implant 100 has been advanced to a position outside of cannula 2108. After advancing ocular implant 100 into Schlemm's canal, the core and the push tube have been retracted into lumen 2184 defined by cannula 2108.

With reference to the figures described above, it will be appreciated that methods in accordance with the present detailed description may be used to position a distal portion of an implant in Schlemm's canal of an eye. An exemplary method in accordance with the present detailed description may include the step of advancing a distal end of a cannula through a cornea of the eye so that a distal portion of the cannula is disposed in the anterior chamber of the eye. The cannula may be used to access Schlemm's canal, for example, by piercing the wall of Schlemm's canal with a distal portion of the cannula.

Methods in accordance with the present detailed description can be used to deliver an implant into Schlemm's canal of an eye. In these exemplary methods, a distal portion of the ocular implant may be advanced out of the distal port of a cannula and into Schlemm's canal. Ocular implant 100 may be disposed on a core while the distal portion of the implant is advanced into Schlemm's canal. In some useful methods, the ocular implant comprises a body defining a plurality of apertures and the method includes the step of closing the apertures with a core. When this is the case, the distal portion of the ocular implant may be advanced into Schlemm's canal while the apertures are closed by the core. Closing the apertures as the ocular implant is advanced into Schlemm's canal may reduce the trauma inflicted on Schlemm's canal by the procedure. Once the ocular implant has reached a desired position, the core may be retracted while a push tube prevents ocular implant from being pulled proximally.

FIG. 25A is a cross sectional view of cannula 2108 sectioned along cutting line A-A shown in FIG. 25C. FIG. 25B is an axial plan view created from the viewpoint illustrated by line B-B in FIG. 25C. FIG. 25C is a plan view showing cannula 2108. FIG. 25A, FIG. 25B, and FIG. 25C may be collectively referred to as FIG. 25.

With reference to FIG. 25, it will be appreciated that cannula 2108 comprises a generally tubular member 2162 having a central axis 2164. In the embodiment of FIG. 25, generally tubular member 2162 comprises a proximal portion 2166, a distal end 2168, and a distal portion 2170 extending between distal end 2168 and proximal portion 2166. In the exemplary embodiment of FIG. 25, proximal portion 2166 is substantially straight, and distal portion 2170 is curved. A distal opening 2169 and distal opening surface 2167 form a tongue 2190. Distal opening 2169 fluidly communicates with a lumen 2184 defined by generally tubular member 2162. With reference to FIG. 25, it will be appreciated that distal portion 2170 is curved in the plane of FIG. 25A and curved in the plane of FIG. 25B.

FIGS. 26 and 27 provide additional views of cannula 2108. Distal opening surface 2167 in tongue 2190 has two sections: a first section 2191 lying in a plane that forms a first section angle greater than 0 degrees and less than 90 degrees with respect to longitudinal axis 2164 of the cannula tube 2162 and a notched section 2192 whose angle with respect to axis 2164 varies from an angle less than that of the first section to an angle greater than the first section.

Figure 28:
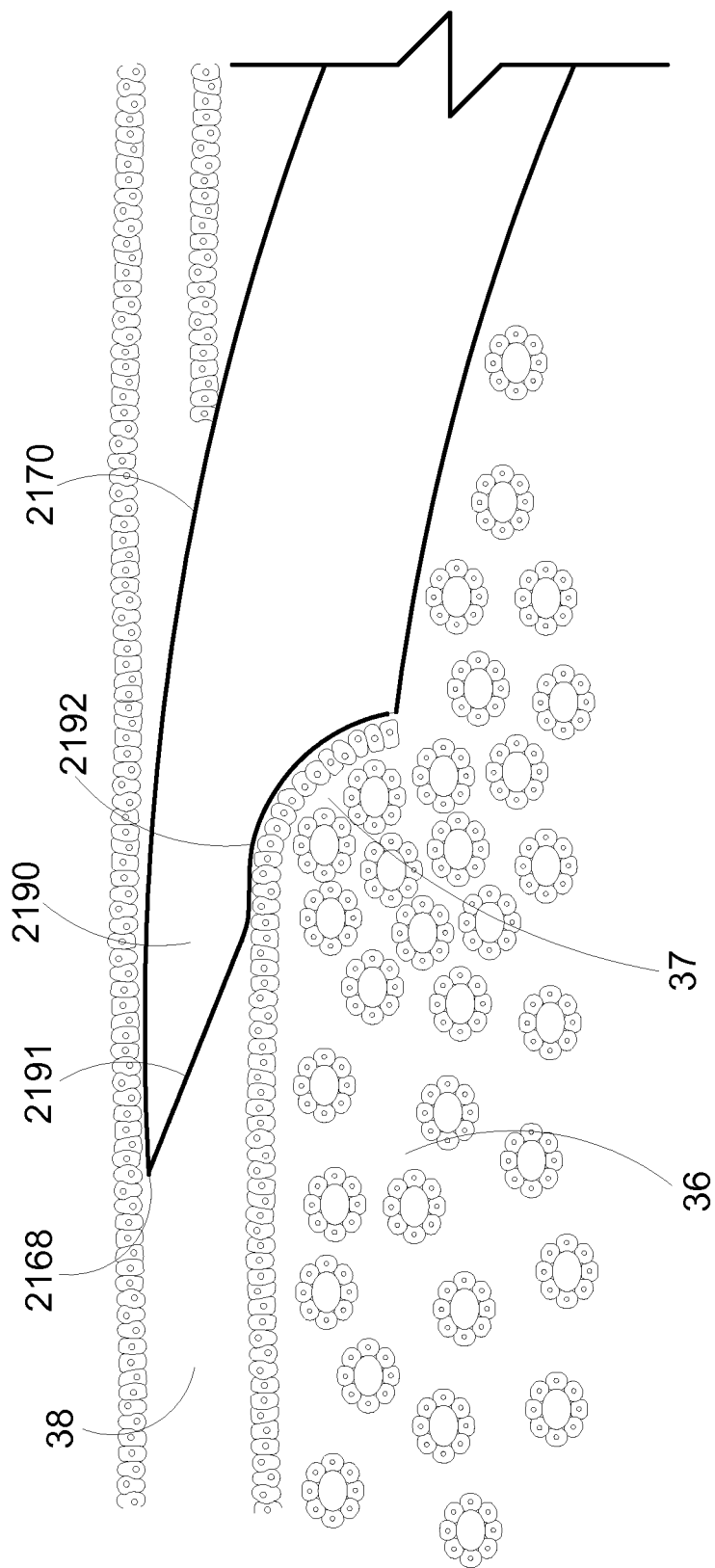
FIG. 28 is a schematic partial cross-sectional view showing the distal tip of an ocular implant delivery system cannula entering Schlemm's canal.

FIG. 28 is a schematic illustration of the use of a ocular implant delivery system cannula. As the distal tip 2168 passes through the trabecular meshwork 36 of the human subject's eye and into Schlemm's canal 38, the distal opening surface of first and second sections 2191 and 2192 of tongue portion 2190 depresses the meshwork and Schlemm's canal tissue in a tenting area 37 to form a transition area for delivery of an ocular implant into Schlemm's canal. As shown, not all of the distal opening of the cannula has been inserted into Schlemm's canal. Instead, tongue 2190 causes the subject's tissue to form a ramp that, together with the inner surface of tongue 2190, guides insertion of the ocular implant into Schlemm's canal.

In addition, since the curve of the cannula at the distal tip 2168 is greater than the curve of Schlemm's canal (i.e., the cannula at its distal end has a smaller radius of curvature than Schlemm's canal), the distal tip may be oriented so that the ocular implant is delivered into the center or possibly slightly radially inward of the outer wall of Schlemm's canal. This combination of cannula shape and cannula orientation helps guide the ocular implant safely into Schlemm's canal.

Figure 29:
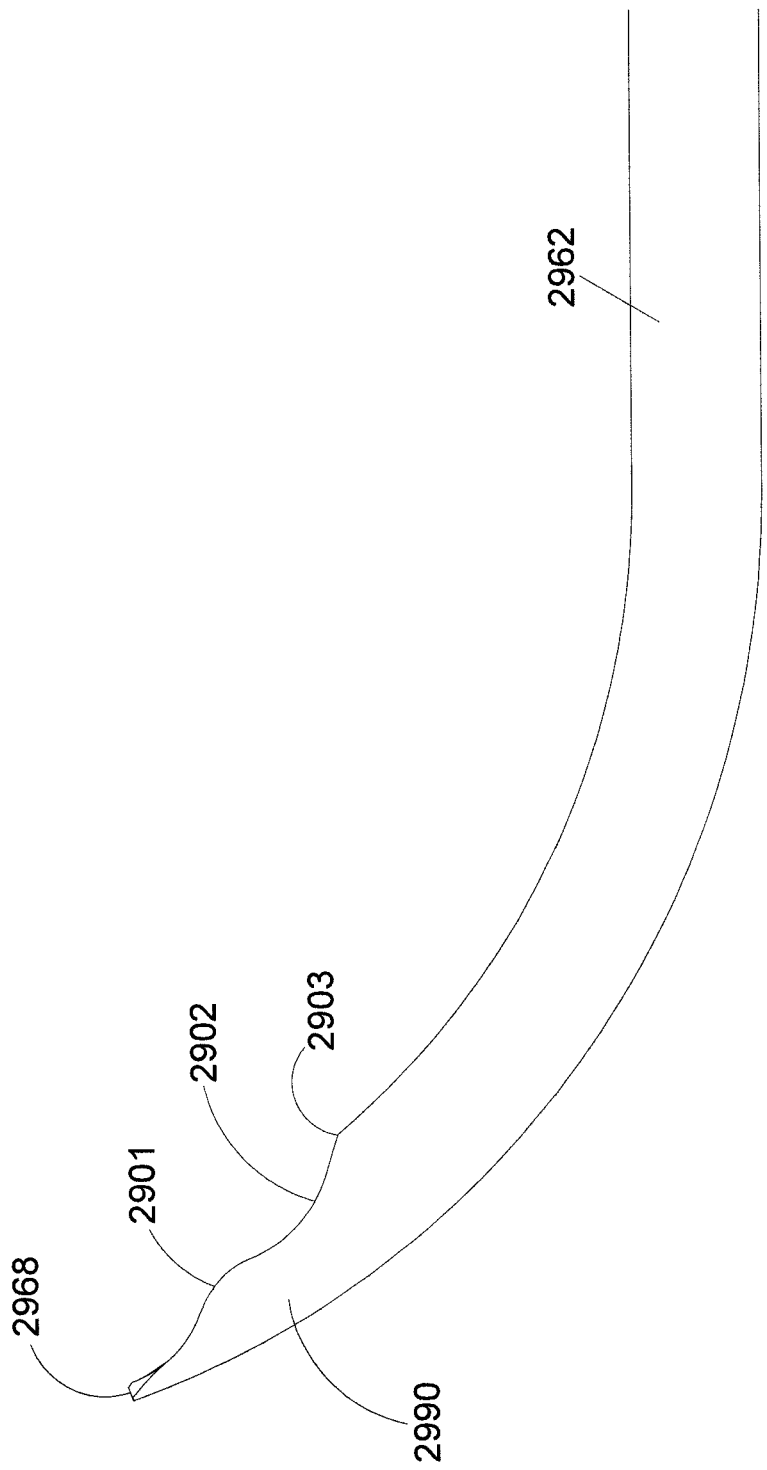
FIG. 29 is a plan view of yet another embodiment of part an ocular implant delivery system cannula.
Figure 30:
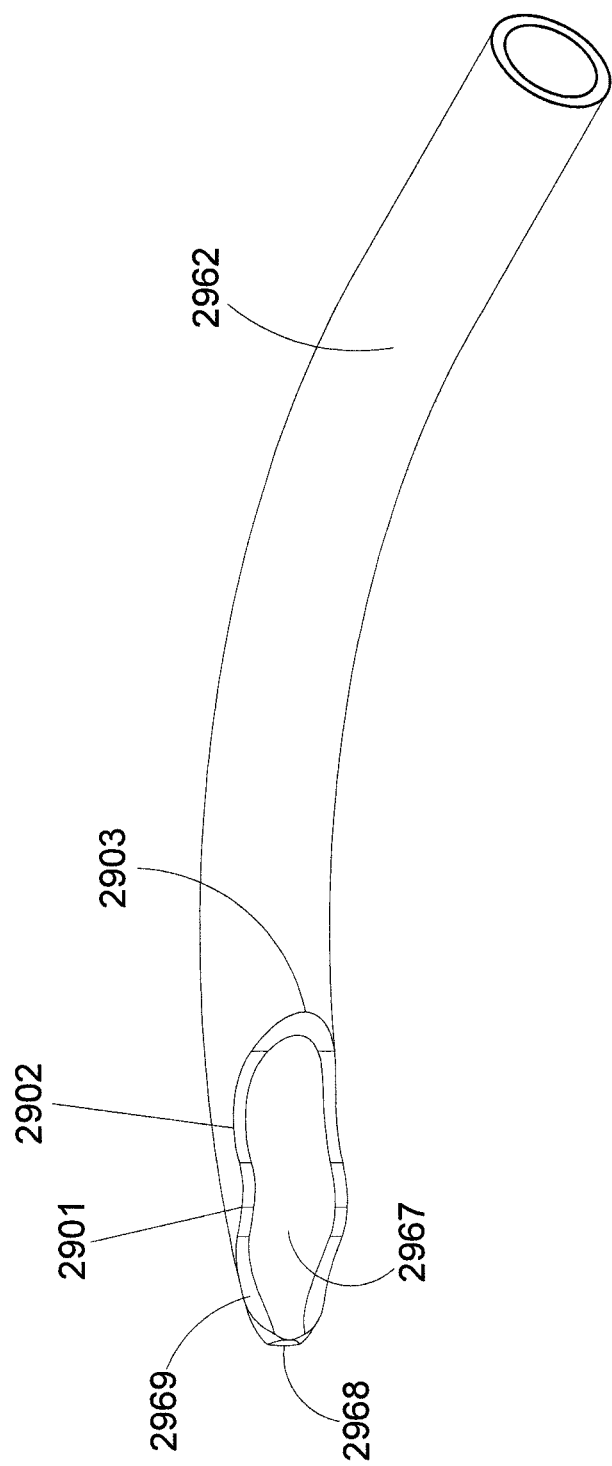
FIG. 30 is a perspective view of a portion of the cannula of FIG. 29.

FIGS. 29 and 30 show yet another embodiment of a cannula tube 2962 for use in an ocular implant delivery system. In this embodiment, a tongue region 2990 extending proximally from the distal tip 2968 of the cannula is defined by a distal opening 2169 and a distal opening surface 2167 with a complex shape. Tube 2962 is formed as a curved cylinder which defines a cylindrical envelope. Tongue 2990 can be described as a region in which the angular extent of material coverage within the cylindrical envelope increases from the distal tip 2968 proximally to a first point 2901, then decreases from point 2901 proximally to a second point 2902, then once again increases from point 2902 proximally to complete 360 degree material coverage within the cylindrical envelope at point 2903.

FIGS. 31-35 show an ocular implant 900 being delivered through yet another embodiment of an ocular implant delivery system cannula 3102 into Schlemm's canal 38. (Schlemm's canal is shown in these figures as being straight instead of curved for ease of illustration.) The ocular implant shown is described in more detail in U.S. application Ser. No. 11/860,318, "Ocular Implants," filed Sep. 24, 2007, now U.S. Pat. No. 7,740,604. It should be understood that other ocular implants may be delivered and deployed by the delivery system of this invention.

Figure 31:
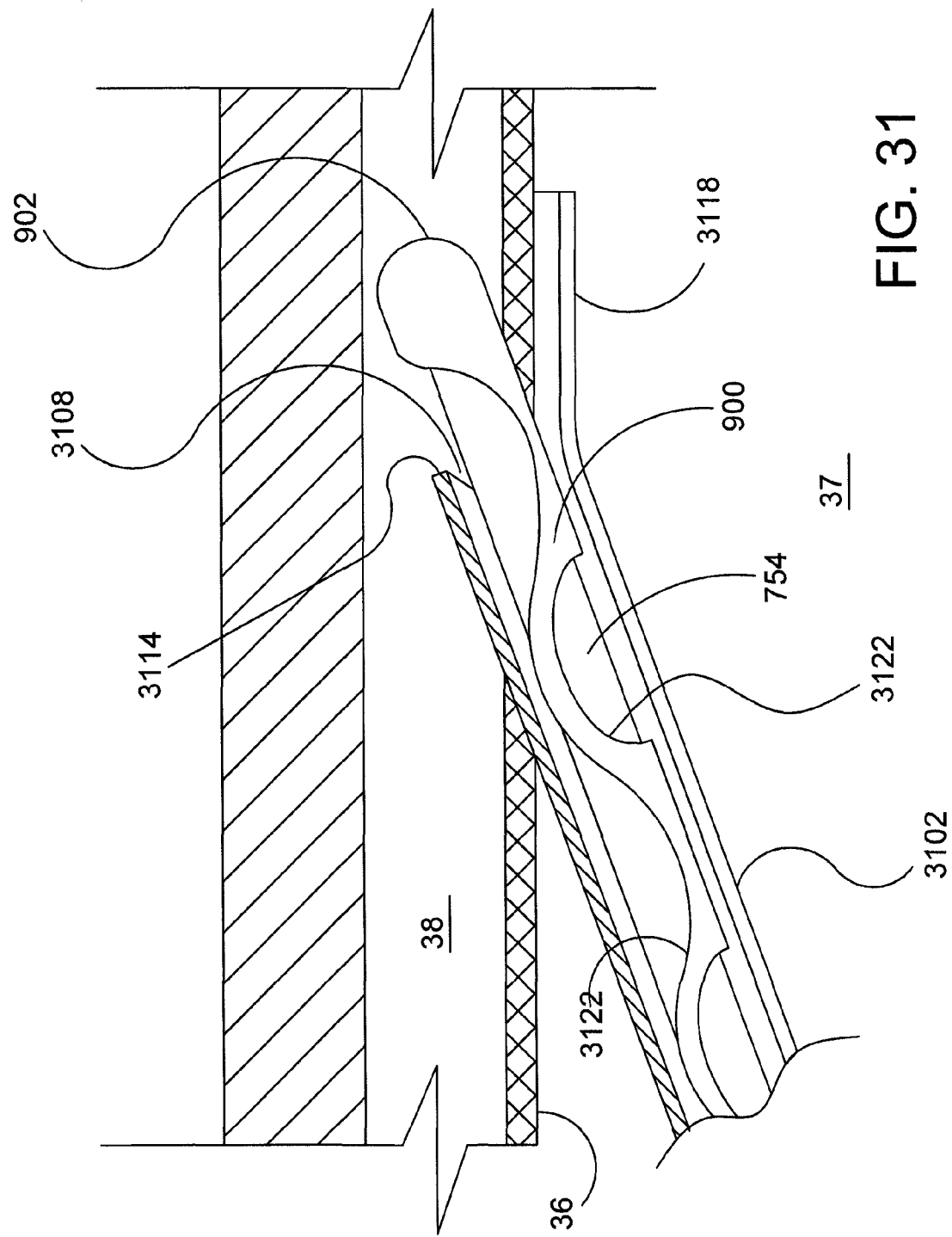
FIG. 31 is a partial cross-sectional view and a partial plan view showing an ocular implant being delivered into Schlemm's canal using still another embodiment of a delivery system cannula according to this invention.
Figure 32:
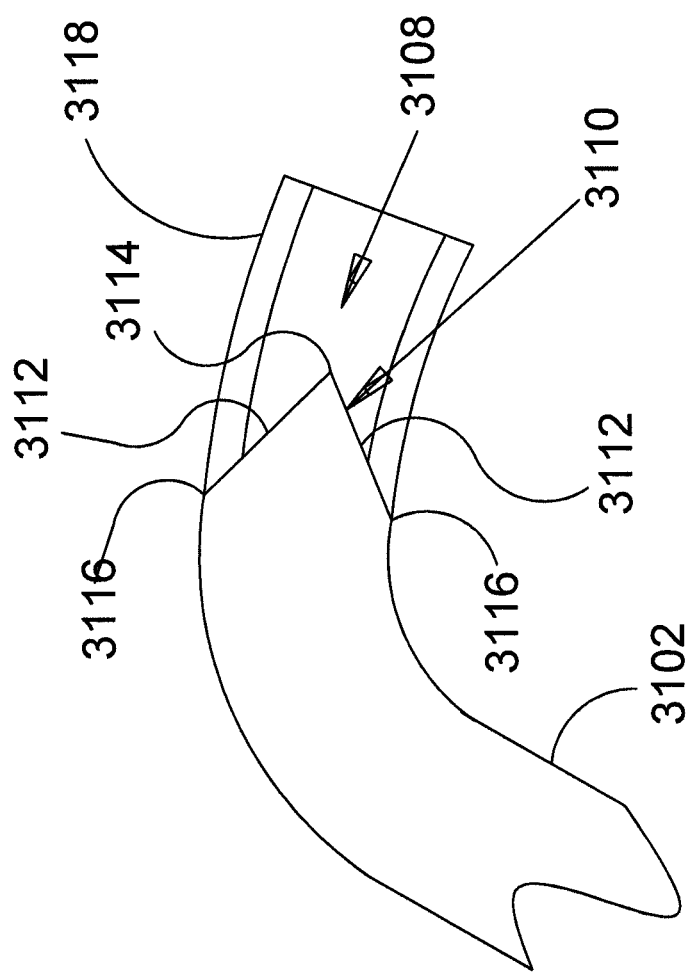
FIG. 32 is an elevational view of a portion of the cannula of the delivery system of FIG. 31.
Figure 33:
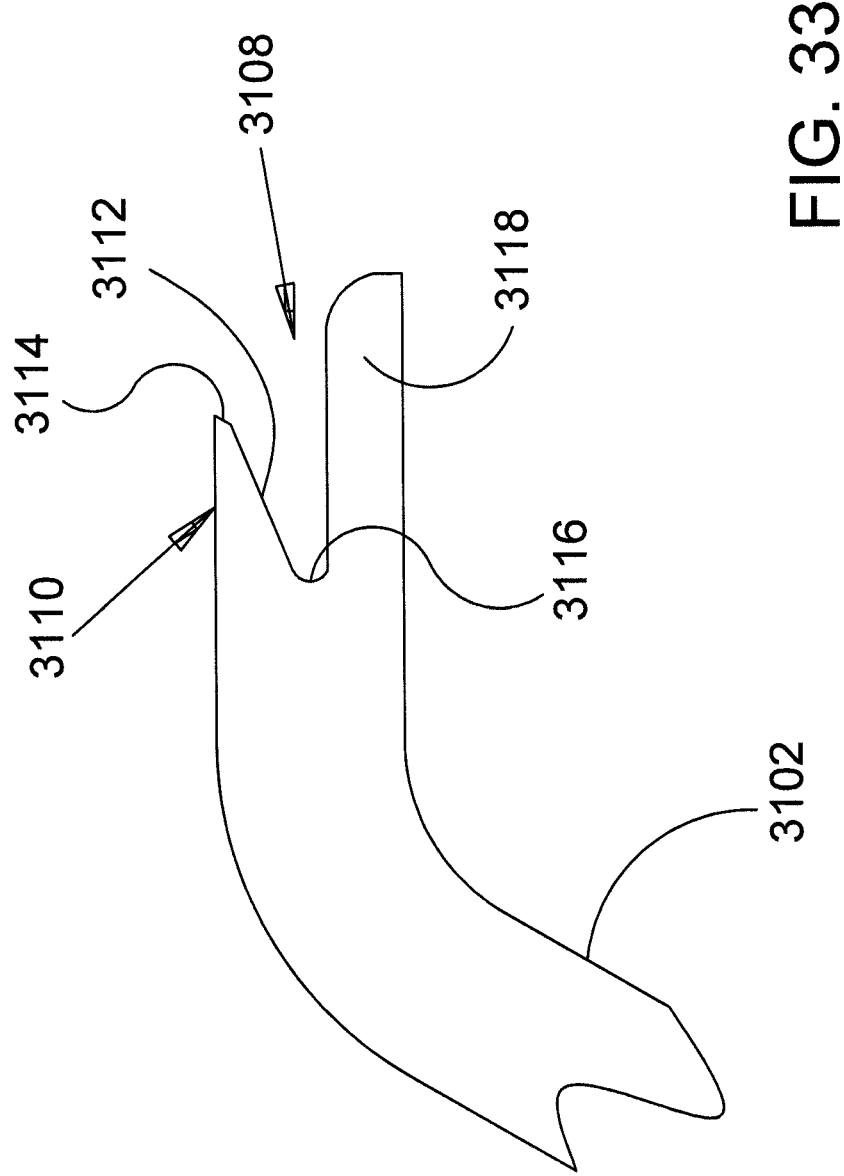
FIG. 33 is a side elevational view of a portion of the cannula of FIG. 32.
Figure 34:
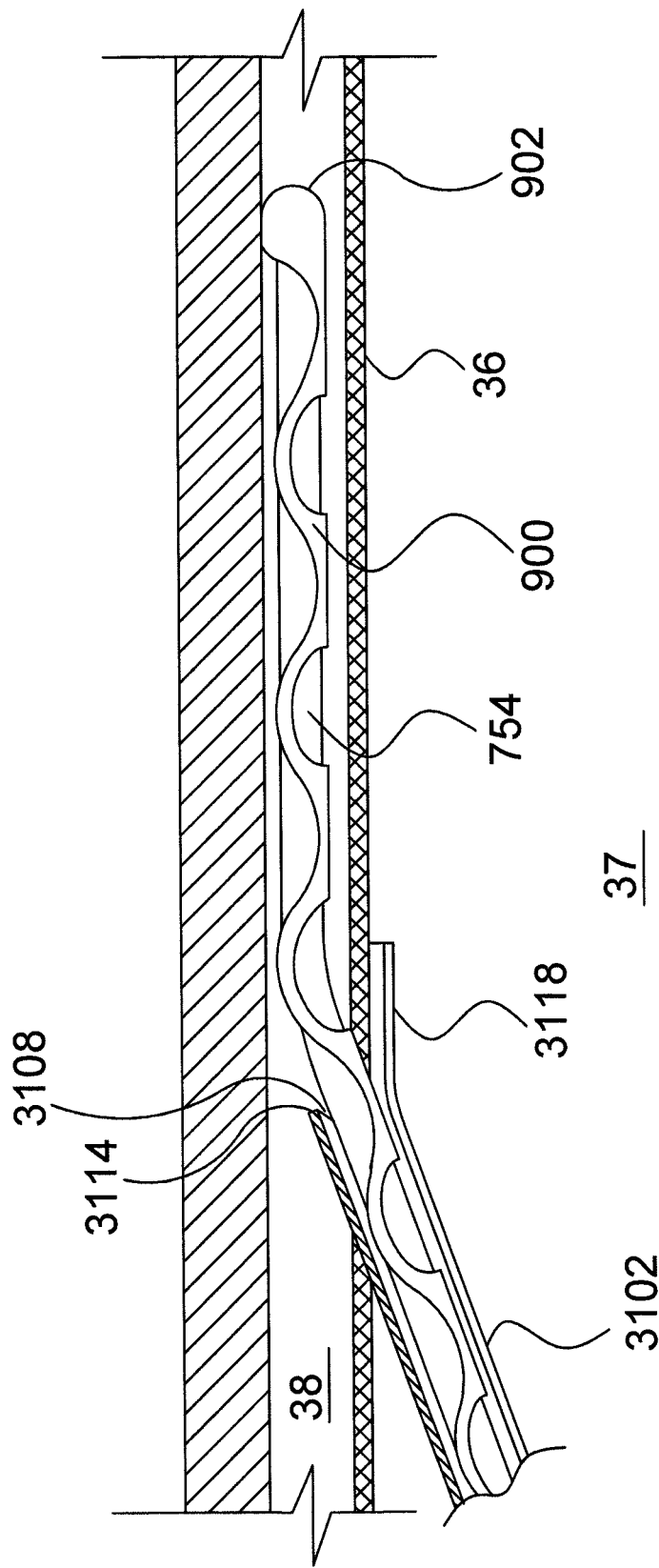
FIG. 34 is a further partial cross-sectional view and partial perspective view showing the ocular implant being delivered into Schlemm's canal using a delivery system cannula according to the embodiment of FIG. 31.
Figure 35:
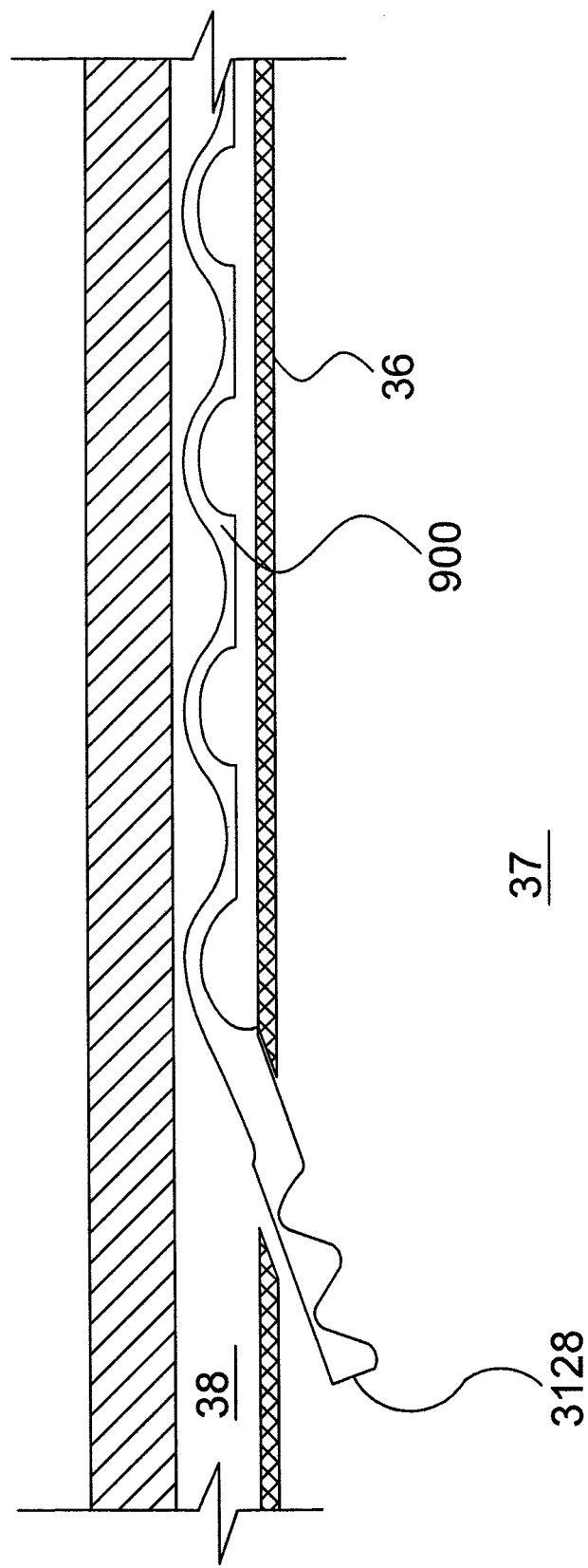
FIG. 35 is a partial cross-sectional view and a partial plan view of an implant in place within Schlemm's canal after delivery.

As shown in FIG. 31, a distal portion of cannula 3102 has passed through the cornea to be within the anterior chamber 37 of the eye and has pierced the trabecular meshwork 36 to enable a distal opening 3108 of cannula 3102 to communicate with Schlemm's canal 38. In this embodiment, cannula 3102 is a rigid curved tube that has a cutting portion 3110 at the distal opening 3108, as shown in more detail in FIGS. 32 and 33. In some embodiments, cannula 3102 is curved to achieve tangential entry into Schlemm's canal, such as by forming an arc of a circle having a radius of curvature less than about 0.1 inches. Other embodiments may have other shapes and curves.

In this embodiment, cutting portion 3110 is formed from two convex edges 3112 meeting at a tip 3114. In other embodiments, the cutting edges can be concave or straight. As shown, edges 3112 extend from tip 3114 to a pair of optional stops 3116 formed at the intersection of edges 3112 with an optional cannula extension portion 3118. As shown in FIG. 31, the distal end of cannula 3102 may be advanced within the anterior chamber 37 toward the trabecular meshwork 36. When the distal end of cannula 3102 meets the trabecular meshwork, tip 3114 and edges 3112 of cutting portion 3110 are advanced to extend through the trabecular meshwork into Schlemm's canal while a tongue or extension portion 3118 bends back and remains within the anterior chamber 37. Distal movement of cannula 3102 ceases when stops 3116 engage the trabecular meshwork.

In some embodiments, cannula 3102 is formed from transparent polycarbonate tubing having a diameter less than about 0.030 inches, e.g., an outer diameter of 0.028 inches and an inner diameter of 0.014 inches. In embodiments with cutting edges leading to stops, the cutting edges may be at angles of between about 10 degrees and 80 degrees with respect to the cannula's central axis, and the stops may be located approximately one-half diameter inward of tip 3114. In embodiments with a cannula extension portion, the extension portion 3118 may extend approximately 1.5 mm beyond tip 3114. Among other functions, the bending of tongue or extension portion 3118 while forward pressure is maintained on the cannula (as shown, e.g., in FIG. 31) provides feedback to the user of robust engagement with the trabecular meshwork and accurate positioning of the distal end of the cannula.

During delivery, ocular implant 900 is mounted on a core or carrier 754 which is movable with implant 000 within cannula 3102. Among other functions, one particular function of core 754 is to block the openings 3122 formed in implant 900 so as to minimize interference between the implant and tissue within Schlemm's canal 38 as the implant is advanced. The ocular implant 900 has a blunt distal end 902 in this embodiment to avoid damage to ocular tissue. In other embodiments, the blunt distal end may be provided at least in part by the carrier.

FIGS. 36A and 36B are section views illustrating an exemplary method in accordance with the present detailed description. The picture plane of FIG. 36A extends laterally across Schlemm's canal SC and the trabecular meshwork 596 overlaying Schlemm's canal SC. In the embodiment of FIG. 36A, the distal end 501 of a cannula 502 has been positioned proximate Schlemm's canal SC. An exemplary method in accordance with the present detailed description may include the step of advancing the distal end of cannula 502 through the cornea of an eye so that a distal portion of cannula 502 is disposed in the anterior chamber 594 of the eye.

FIG. 36B is an additional section view showing Schlemm's canal SC shown in the previous figure. In FIG. 36, a distal end 501 of cannula 502 is shown extending through a wall of Schlemm's canal SC and trabecular meshwork 596. A distal opening 504 of cannula 502 fluidly communicates with Schlemm's canal in the embodiment of FIG. 36B.

While exemplary embodiments of the present invention have been shown and described, modifications may be made, and it is therefore intended in the appended claims to cover all such changes and modifications which fall within the true spirit and scope of the invention.

What is claimed is:

1. An ocular implant and delivery system comprising:
an ocular implant comprising a body, an elongate channel extending longitudinally within the body, a proximal inlet in fluid communication with the elongate channel, a distal outlet in fluid communication with the elongate channel, and a plurality of openings disposed between the proximal inlet and the distal outlet and communicating with the elongate channel; and a delivery system comprising a core adapted to be disposed within the ocular implant to block the plurality of implant openings when the implant is mounted on the core, the core having a blunt distal end, the core being operable from outside an eye to advance the distal end of the ocular implant from an anterior chamber of the eye through tissue adjacent the anterior chamber to dispose the implant proximal inlet in the anterior chamber and the distal end outside of the anterior chamber and to thereafter be withdrawn from the implant and from the eye.

2. The system of claim 1 wherein the delivery system further comprises a cannula, the core being disposed within and extending from the cannula.

3. The system of claim 2 wherein the delivery system further comprises a hub at a proximal end of the cannula.

4. The system of claim 1 wherein the core is further adapted to extend through the implant proximal inlet and inlet distal outlet during delivery of the implant to the eye.

* * * * *